United States Patent
Borody

(10) Patent No.: US 9,901,604 B2
(45) Date of Patent: *Feb. 27, 2018

(54) PROBIOTIC RECOLONISATION THERAPY

(71) Applicant: Crestovo Holdings LLC, Greenwich, CT (US)

(72) Inventor: Thomas Julius Borody, Five Dock (AU)

(73) Assignee: Crestovo Holdings LLC, Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/017,376

(22) Filed: Feb. 5, 2016

(65) Prior Publication Data

US 2016/0151432 A1    Jun. 2, 2016

Related U.S. Application Data

(60) Continuation of application No. 14/793,630, filed on Jul. 7, 2015, now Pat. No. 9,320,763, and a
(Continued)

(30) Foreign Application Priority Data

Jul. 25, 2000 (AU) .................................. PQ8997

(51) Int. Cl.
*A61K 45/00* (2006.01)
*A01N 63/00* (2006.01)
*A61M 36/14* (2006.01)
*A61K 9/16* (2006.01)
*A61K 9/50* (2006.01)
*A61K 35/742* (2015.01)
*A61K 35/74* (2015.01)
*A61K 38/48* (2006.01)
*A61K 35/741* (2015.01)
*A61K 35/744* (2015.01)
(Continued)

(52) U.S. Cl.
CPC ............ *A61K 35/742* (2013.01); *A23C 9/123* (2013.01); *A23C 9/127* (2013.01); *A23C 9/13* (2013.01); *A23L 2/52* (2013.01); *A23L 33/135* (2016.08); *A61K 9/0031* (2013.01); *A61K 9/0053* (2013.01); *A61K 9/19* (2013.01); *A61K 9/48* (2013.01); *A61K 9/4891* (2013.01); *A61K 9/50* (2013.01); *A61K 9/5005* (2013.01); *A61K 31/341* (2013.01); *A61K 31/41* (2013.01); *A61K 31/495* (2013.01); *A61K 31/7034* (2013.01); *A61K 35/24* (2013.01); *A61K 35/37* (2013.01); *A61K 35/38* (2013.01); *A61K 35/74* (2013.01); *A61K 35/741* (2013.01); *A61K 35/744* (2013.01); *A61K 35/745* (2013.01); *A61K 35/747* (2013.01); *A61K 36/062* (2013.01); *A61K 38/14* (2013.01); *A61K 38/4893* (2013.01); *A61K 45/06* (2013.01); *A23V 2002/00* (2013.01); *A61K 9/5078* (2013.01); *A61K 31/43* (2013.01); *A61K 31/545* (2013.01); *A61K 31/7048* (2013.01); *A61K 35/76* (2013.01); *A61K 38/00* (2013.01); *A61K 39/00* (2013.01); *A61K 39/39* (2013.01); *A61K 51/1217* (2013.01); *A61K 2035/115* (2013.01); *C12N 2795/00032* (2013.01)

(58) Field of Classification Search
CPC ...... A61K 39/39; A61K 35/74; A61K 35/742; A61K 51/1217; A61K 9/0578
See application file for complete search history.

(56) References Cited

U.S. PATENT DOCUMENTS

| 3,192,116 A | 6/1965 | Möse et al. |
| 3,320,130 A | 5/1967 | Henry |

(Continued)

FOREIGN PATENT DOCUMENTS

| AU | 2001276160 B2 | 6/2007 |
| CA | 1333564 | 12/1994 |

(Continued)

OTHER PUBLICATIONS

Andrews et al., The Medical Journal of Australia, 1993; 159: 633-634.*

(Continued)

*Primary Examiner* — Gary Nickol
*Assistant Examiner* — Lakia Jackson-Tongue
(74) *Attorney, Agent, or Firm* — Arnold & Porter Kaye Scholer LLP; David R. Marsh

(57) ABSTRACT

The present invention relates to pharmaceutical compositions suitable for the treatment of chronic diseases associated with the presence of abnormal or an abnormal distribution of microflora in the gastrointestinal tract of a mammalian host, which compositions comprise viable non-pathogenic or attenuated pathogenic Clostridia. The compositions further comprise one or more additional viable non-pathogenic or attenuated pathogenic microorganisms selected from the group consisting of *Bacteroides*, Eubacteria, Fusobacteria, Propionibacteria, Lactobacilli, anaerobic cocci, *Ruminococcus, E. coli, Gemmiger, Desulfomonas, Peptostreptococcus*, and fungi. The present invention also provides pharmaceutical compositions suitable for the treatment of the same chronic diseases comprising viable non-pathogenic or attenuated pathogenic *Escherichia coli*, at least one strain of viable non-pathogenic or attenuated pathogenic *Bacteroides* and at least one strain of viable non-pathogenic or attenuated pathogenic microorganism.

37 Claims, No Drawings

Related U.S. Application Data continuation of application No. 14/793,642, filed on Jul. 7, 2015, now Pat. No. 9,408,872, and a continuation of application No. 14/793,623, filed on Jul. 7, 2015, now Pat. No. 9,468,658, and a continuation of application No. 14/710,487, filed on May 12, 2015, and a continuation of application No. 14/710,481, filed on May 12, 2015, said application No. 14/793,630 is a continuation of application No. 14/710,487, filed on May 12, 2015, and a continuation of application No. 14/710,481, filed on May 12, 2015, said application No. 14/793,642 is a continuation of application No. 14/710,487, filed on May 12, 2015, and a continuation of application No. 14/710,481, filed on May 12, 2015, said application No. 14/793,623 is a continuation of application No. 14/710,487, filed on May 12, 2015, and a continuation of application No. 14/710,481, filed on May 12, 2015, which is a continuation of application No. 14/270,034, filed on May 5, 2014, now Pat. No. 9,050,358, and a continuation of application No. 13/910,579, filed on Jun. 5, 2013, now Pat. No. 9,040,036, said application No. 14/710,487 is a continuation of application No. 14/270,034, filed on May 5, 2014, now Pat. No. 9,050,358, and a continuation of application No. 13/910,579, filed on Jun. 5, 2013, now Pat. No. 9,040,036, said application No. 14/270,034 is a continuation of application No. 13/910,579, filed on Jun. 5, 2013, now Pat. No. 9,040,036, which is a division of application No. 10/332,986, filed as application No. PCT/AU01/00907 on Jul. 25, 2001, now Pat. No. 8,460,648.

(51) Int. Cl.

| | | |
|---|---|---|
| A61K 35/747 | (2015.01) | |
| A61K 36/062 | (2006.01) | |
| A61K 45/06 | (2006.01) | |
| A61K 38/14 | (2006.01) | |
| A61K 31/341 | (2006.01) | |
| A61K 31/41 | (2006.01) | |
| A61K 31/495 | (2006.01) | |
| A61K 31/7034 | (2006.01) | |
| A23L 2/52 | (2006.01) | |
| A61K 35/745 | (2015.01) | |
| A61K 35/38 | (2015.01) | |
| A61K 35/24 | (2015.01) | |
| A61K 9/00 | (2006.01) | |
| A23C 9/123 | (2006.01) | |
| A61K 9/48 | (2006.01) | |
| A23C 9/13 | (2006.01) | |
| A23L 33/135 | (2016.01) | |
| A23C 9/127 | (2006.01) | |
| A61K 9/19 | (2006.01) | |
| A61K 35/37 | (2015.01) | |
| A61K 31/545 | (2006.01) | |
| A61K 39/00 | (2006.01) | |
| A61K 35/76 | (2015.01) | |
| A61K 31/43 | (2006.01) | |
| A61K 38/00 | (2006.01) | |
| A61K 31/7048 | (2006.01) | |
| A61K 39/39 | (2006.01) | |
| A61K 51/12 | (2006.01) | |
| A61K 35/00 | (2006.01) | |

(56) References Cited

U.S. PATENT DOCUMENTS

| | | | |
|---|---|---|---|
| 3,713,836 A | 1/1973 | Carlsson | |
| 4,098,728 A | 7/1978 | Rosenblatt | |
| 4,332,790 A | 6/1982 | Sozzi et al. | |
| 4,335,107 A | 6/1982 | Snoeyenbos et al. | |
| 4,452,779 A | 6/1984 | Cockerill | |
| 4,536,409 A | 8/1985 | Farrell et al. | |
| 4,657,762 A | 4/1987 | Mikkola et al. | |
| 4,710,379 A | 12/1987 | Kawai et al. | |
| 4,892,731 A | 1/1990 | Arai et al. | |
| 4,975,286 A | 12/1990 | Hechter | |
| 5,213,807 A | 5/1993 | Chemburkar et al. | |
| 5,266,315 A | 11/1993 | Taguchi et al. | |
| 5,443,826 A * | 8/1995 | Borody | A61K 35/74 424/543 |
| 5,599,795 A | 2/1997 | McCann et al. | |
| 5,728,380 A | 3/1998 | Allen et al. | |
| 5,800,821 A | 9/1998 | Acheson et al. | |
| 5,837,238 A | 11/1998 | Casas et al. | |
| 5,858,356 A | 1/1999 | Wolf et al. | |
| 5,902,578 A | 5/1999 | Halpin-Dohnalek et al. | |
| 5,902,743 A | 5/1999 | Luchansky et al. | |
| 6,087,386 A | 7/2000 | Chen et al. | |
| 6,162,464 A | 12/2000 | Jacob et al. | |
| 6,245,740 B1 | 6/2001 | Goldenberg et al. | |
| 6,284,274 B1 | 9/2001 | Merrill et al. | |
| 6,428,783 B1 | 8/2002 | Khachatrian et al. | |
| 6,514,531 B1 | 2/2003 | Alaux et al. | |
| 6,645,530 B1 | 11/2003 | Borody | |
| 6,649,397 B1 | 11/2003 | Nakamura | |
| 6,756,032 B1 * | 6/2004 | Tepper | A61K 49/0006 424/9.8 |
| 6,926,907 B2 | 8/2005 | Plachetka | |
| 6,979,674 B1 | 12/2005 | Goldenberg et al. | |
| 6,984,513 B2 | 1/2006 | Brown et al. | |
| 7,018,629 B2 | 3/2006 | Jacob et al. | |
| 7,374,753 B1 | 5/2008 | Farmer et al. | |
| 7,541,091 B2 | 6/2009 | Sisson et al. | |
| 7,749,509 B2 | 7/2010 | Cobb et al. | |
| 7,763,276 B1 | 7/2010 | Shodai et al. | |
| 7,799,341 B2 | 9/2010 | Porzio et al. | |
| 7,815,956 B2 | 10/2010 | Lee et al. | |
| 7,846,475 B2 | 12/2010 | Shiraishi et al. | |
| 7,888,062 B1 | 2/2011 | Garner et al. | |
| 7,998,510 B2 | 8/2011 | Caswell | |
| 8,168,171 B2 | 5/2012 | Mogna et al. | |
| 8,460,648 B2 | 6/2013 | Borody | |
| 8,637,297 B2 | 1/2014 | Fernandez et al. | |
| 8,658,153 B2 | 2/2014 | Daube et al. | |
| 8,771,673 B2 | 7/2014 | Cobb et al. | |
| 9,040,036 B2 * | 5/2015 | Borody | A23L 1/3014 424/239.1 |
| 9,050,538 B2 | 6/2015 | Borody | |
| 9,308,226 B2 | 4/2016 | Borody | |
| 9,320,763 B2 | 4/2016 | Borody | |
| 9,408,872 B2 * | 8/2016 | Borody | A61K 35/741 |
| 9,468,658 B2 | 10/2016 | Borody | |
| 9,572,841 B2 | 2/2017 | Borody | |
| 9,572,842 B2 | 2/2017 | Borody | |
| 9,610,308 B2 | 4/2017 | Borody | |
| 2001/0014322 A1 | 8/2001 | Chen et al. | |
| 2002/0013270 A1 | 1/2002 | Bolte | |
| 2002/0022019 A1 | 2/2002 | Laulund | |
| 2002/0039599 A1 | 4/2002 | Lin et al. | |
| 2003/0092163 A1 | 5/2003 | Collins et al. | |
| 2003/0092724 A1 | 5/2003 | Kao et al. | |
| 2003/0147858 A1 | 8/2003 | Renaud et al. | |
| 2004/0062757 A1 | 4/2004 | Finegold | |
| 2004/0167062 A1 | 8/2004 | Bolte | |
| 2004/0170617 A1 | 9/2004 | Finegold | |
| 2004/0223956 A1 | 11/2004 | Naidu et al. | |
| 2006/0076536 A1 | 4/2006 | Barshied | |
| 2006/0099197 A1 | 5/2006 | Farmer | |
| 2006/0115465 A1 | 6/2006 | MacFarlane et al. | |
| 2006/0275223 A1 | 12/2006 | Burr | |
| 2007/0059296 A1 | 3/2007 | Chen | |

(56) References Cited

U.S. PATENT DOCUMENTS

| | | |
|---|---|---|
| 2008/0254009 A1 | 10/2008 | Finegold |
| 2008/0299197 A1 | 12/2008 | Toneguzzo et al. |
| 2010/0112003 A1 | 5/2010 | Collins et al. |
| 2010/0178349 A1 | 7/2010 | Koller et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookawa et al. |
| 2010/0239667 A1 | 9/2010 | Hemmingsen et al. |
| 2010/0247489 A1 | 9/2010 | Saur-Brosch et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Ubeda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0200570 A1 | 8/2011 | Mosbaugh et al. |
| 2011/0218216 A1 | 9/2011 | Vivek et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0183612 A1 | 7/2012 | Brogmann et al. |
| 2012/0252775 A1 | 10/2012 | Finegold |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 11/2014 | Allen-Vercoe et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1* | 10/2015 | Borody ............... A23L 1/3014 424/463 |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151433 A1 | 6/2016 | Borody |
| 2016/0158294 A1 | 6/2016 | Von Maltzahn et al. |
| 2016/0279178 A1 | 9/2016 | Borody |
| 2016/0279179 A1 | 9/2016 | Borody |

FOREIGN PATENT DOCUMENTS

| | | |
|---|---|---|
| CA | 2 391 422 A1 | 1/2004 |
| CN | 1561387 A | 1/2005 |
| CN | 201441672 U | 4/2010 |
| DE | 2 134 179 A1 | 1/1973 |
| EP | 0 303 426 A2 | 2/1989 |
| EP | 0 456 418 A2 | 11/1991 |
| EP | 0 433 299 B1 | 5/1998 |
| EP | 1 514 572 A2 | 3/2005 |
| EP | 1 800 688 A1 | 6/2007 |
| EP | 1 514 572 B1 | 12/2008 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1 271 674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |
| JP | 2010-520234 A | 6/2010 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 00/015760 | 3/2000 |
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |
| WO | WO 2011/110347 A2 | 9/2011 |
| WO | WO 2011/152566 A2 | 12/2011 |
| WO | WO 2012/016287 A2 | 2/2012 |
| WO | WO 2012/045150 A1 | 4/2012 |
| WO | WO 2012/122478 A1 | 9/2012 |
| WO | WO 2012/016287 A3 | 11/2012 |
| WO | WO 2011/151941 A1 | 12/2012 |
| WO | WO 2013/037067 A1 | 3/2013 |
| WO | WO 2013/090825 A1 | 6/2013 |
| WO | WO 2014/152338 A1 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |

OTHER PUBLICATIONS

Taras et al., "Reclassification of Eubacterium formicigenerans Holdeman and Moore 1974 as Dorea formicigenerans gen. nov., coomb. nov., and description of Dorea longicatena sp. nov., isolated from human faeces," International Journal of Systematic and Evolutionary Microbiology, 52:423-428 (2002).

Agrawal et al., "'Global warming' to Mycobacterium avium subspecies paratuberculosis," Future Microbiol, 9(7):829-832 (2014).

Agrawal et al., "A Long-Term Follow-Up Study of the Efficacy and Safety of Fecal Microbiota Transplant (FMT) for Recurrent/Severe/Complicated C. difficile Infection (CDI) in the Elderly," Gastroenterol, 146(5)(Suppl 1):S42-43 (2014).

Aitken et al., "Demonstration of Intracellular Mycobacterium Species in Crohn's Disease Using Novel Technologies," Poster Presentation—2015 ACG Annual Scientific Meeting, Honolulu, Hawaii, USA (2015).

Akao et al., "A Purgative Action of Barbaloin Is Induced by Eubacterium sp. Strain BAR, a Human Intestinal Anaerobe, Capable of Transforming Barbaloin to Aloe-Emodin Anthrone," Biol. Pharm., 19(1):136-138 (1996).

Andrews et al., "Bacteriotherapy for Chronic Constipation—A Long Term Follow-Up," Gastroenterol, 108:A563 Abstract (1995).

(56) References Cited

OTHER PUBLICATIONS

Andrews et al., "Chronic Constipation (CC) may be reversed by Bacteriotherapy," *Gastroenterol*, 106:A459 (1994).
Andrews et al., "Chronic constipation reversed by restoration of bowel flora. A case and a hypothesis," *European Journal of Gastroenterology & Hepatology*, 4:245-247 (1992).
Aroniadis et al., "Long-Term Follow-up Study of Fecal Microbiota Transplantation (FMT) for Severe or Complicated Clostridium difficile Infection (CDI)," *Gastroenterol*, 144(Suppl 1):S185 (2013).
Borody et al., "The GI Microbiome and its Role in Chronic Fatigue Syndrome: a Summary of Bacteriotherapy," *ACNEM Journal*, 31(3):3-8 (2012).
Borody et al., "Anti-MAP Rescues Anti-TNF Failures for Over 4 Years," *Gastroenterol*, 136(5)Suppl 1:A-681 (2009).
Borody et al., "Anti-MAP Therapy for Pediatric Crohn's Disease," *Am J Gastroenterol*, 108(Suppl 1):S516 (2013).
Borody et al., "Anti-MAP Therapy in the Treatment of Active Crohn's Disease," *J Gastroenterol & Hepatol*, 20(Suppl):A2 (2005).
Borody et al., "Anti-mycobacterial therapy in Crohn's disease heals mucosa with longitudinal scars," *Digestive & Liver Disease*, 39(5):438-444 (2007).
Borody et al., "Anti-*Mycobacterium avium* SS *paratuberculosis* (MAP) Therapy and Fistula Closure in Patients with Severe Crohn's Disease," *Am J Gast*, A101: S440 (2006).
Borody et al., "Bacteriotherapy in Chronic Fatigue Syndrome (CFS): A retrospective review," *Am J Gastro*, 107(S1):A1481 (2012).
Borody et al., "Changes in Crohn's Disease Activity Index and C-Reactive Protein Levels During Anti-MAP Therapy," *AM J Gastro*, 104(S3):A1293 (2009).
Borody et al., "Clostridium difficile Complicating Inflammatory Bowel Disease: Pre- and Post-Treatment Findings," *Gastroenterol*, 134(4)Suppl 1:A-361 (2008).
Borody et al., "Could fecal microbiota transplantation cure all Clostridium difficile infections?," *Future Microbiol*, 9:1-3 (2014).
Borody et al., "Entamoeba histolytica: another cause of Crohn's Disease," *AM J Gastro*, 104(S3):A990 (2009).
Borody et al., "Faecal bacteriotherapy (FB) for chronic C. difficile (Cd) syndromes," *J Gastroenterol Hepatol*, 18(Suppl.):B8 (Abstract) (2003).
Borody et al., "Fecal bacteriotherapy in the treatment of recurrent C. difficile infection," *UpToDate*, pp. 1-6 (2006).
Borody et al., "Fecal Microbiota Transplantation (FMT) in Multiple Sclerosis (MS)," *AM J Gastro*, 106(S2):A942 (2011).
Borody et al., "Fecal microbiota transplantation for Clostridium difficile infection: A surgeon's perspective" *Seminars in Colon and Rectal Surgery*, 25:163-166 (2014).
Borody et al., "Fecal microbiota transplantation in gastrointestinal diseases—What practicing physcians should know," *Polish Archives of Internal Medicine*, 125(11):852-858 (2015).
Borody et al., "Fecal microbiota transplantation in the treatment of recurrent Clostridium difficile infection," *UpToDate*, pp. 1-4, (2015).
Borody et al., "Fecal Microbiota Transplantation in Ulcerative Colitis: Review of 24 Years Experience," *Am J Gastro*, 107(Supp 1):A1644 (2012).
Borody et al., "Fecal microbiota transplantation: a new standard treatment option for Clostridium difficile infection," *Expert Rev Anti Infect Ther.*, 11(5):447-449 (2013).
Borody et al., "Fecal Microbiota Transplantation. Expanding Horizons for Clostridium difficile Infections and Beyond," *Antibiotics*, 4:254-266 (2015).
Borody et al., "Fecal Microbiota Transplantation. Indications, Methods, Evidence, and Future Directions," *Curr Gastroenterol Rep*, 15:337-344 (2013).
Borody et al., "Fecal Microbiota Transplantation: Techniques, Applications, and Issues," *Gastroenterol Clin North Am*, 41:781-803 (2012).
Borody et al., "Irritable Bowel Syndrome and Dientamoeba Fragilis," *ASM Sydney National Conference*, pp. 4-5 (2002).
Borody et al., "Is Crohn's Disease Ready for Fecal Microbiota Transplantation?,"*J Clin Gastroenterol*, 48(7):582-583 (2014).
Borody et al., "Myoclonus-dystonia affected by GI Microbiota?,"*AM J Gastro*, 106(S2):A940 (2011).
Borody et al., "Novel appearance of healing mucosa following anti-*Mycobacterium avium paratuberculosis* therapy for Crohn's disease," *J Gastroenterol Hepatol*, 19(Suppl):A210 (2004).
Borody et al., Reversal of Idiopathic Thrombocytopenic Purpura [ITP] with Fecal Microbiota Transplantation [FMT],*AM J Gastro*, 106(S2):A941 (2011).
Borody et al., "Reversal of Inflammatory Bowel Disease (IBD) with Recurrent Faecal Microbiota Transplants (FMT)," *AM J Gastro*, 106(S2):A979 (2011).
Borody et al., "Severe recurrent Crohn's Disease of ileocolonic anastomosis and antimicrobial (anti-mycobacterial therapy)," *Gut*, 55:1211 (2006).
Borody et al., "Therapeutic faecal microbiota transplantation: current status and future developments," *Curr Opin Gastroenterol*, 30:97-105 (2014).
Borody et al., "Treatment of chronic constipation and colitis using human probiotic infusions," *Proceedings of Prebiotics and Probiotics and the New Foods Conference*, 2-4:228 Abstract (2001).
Borody et al., "Treatment of First-time Clostridium difficile Infection with Fecal Microbiota Transplantation," Poster Presentation, 2015 ACG Annual Scientific Meeting, Honolulu, Hawaii, USA (2015).
Borody et al., "Treatment of Severe Constipation Improves Parkinson's Disease (PD) Symptoms," *AM J Gastro*, 104(S3):A999 (2009).
Borody et al., "Treatment of Severe Crohn's Disease (CD)—Using Rifabutin-Macrolide-Clofazimine Combination: Results at 30-37 Months," *Gastroenterology*, 118(4):A1334 Abstract (2000).
Borody et al., Treatment of Severe Crohn's Disease Using Rifabutin-Macrolide-Clofazimine Combination—Results at 38-43 Months, *J Gastroenterol & Hepatol*, 15(Suppl.):J102 (2000).
Borody et al., "Treatment of severe Crohn's disease using antimycobacterial triple therapy—approaching a cure?," *Digest Liver Dis*, 34(1):29-38 (2002).
Borody, "Bacteriotherapy for Chronic Fatigue Syndrome—A Long Term Follow-Up Study," *Proceedings of ACMA Complementary Medicine Sydney*, p. 1 (1995).
Borody, "Flora Power—Fecal Bacteria Cure Chronic C. difficile Diarrhoea," *Am J Gastroenterol*, 95(11):3028-3029 (2000).
Borody, "Is the Infected Patient too 'Difficile'to Treat?," The Australian Society Microbiology 2009 Perth, SY03 & SY03.1, p. 27 & 56, (2009).
Borody, "Letter to the Editor—Response to Drs. Famularo et al.," AJG, 96(7):2262-2264 (2001).
Brandt et al., Safety of Fecal Microbiota Transplantation (FMT) in Immunocompromised (Ic) Patients with Inflammatory Bowel Disease (IBD), *Am J Gastroenterol*, 108(Suppl 1):S556 (2013).
Campbell et al., "The many faces of Crohn's Disease: Latest concepts in etiology," *OJIM*, 2(2):107-115 (2012).
Chamberlain et al., "MAP-associated Crohn's Disease, MAP, Koch's postulates, causality and Crohn's Disease," *Digestive and Liver Disease*, 39:790-794 (2007).
Chamberlin et al., "Primary treatment of Crohn's disease: combined antibiotics taking center stage," *Expert Rev. Clin. Immunol.*, 7(6):751-760 (2011).
Clancy et al., "Anti-MAP Therapy Induces and Maintains Remission in Severe Crohn's Disease," *Ann NY Acad Sci*, p. 1 (2005).
Gitlin et al., "*Mycobacterium avium* ss *paratuberculosis*-associated Diseases: Piecing the Crohn's Puzzle Together," *J Clin Gastroenterol*, 46(8):649-655 (2012).
Henriksson et al., "Probiotics under the regulatory microscope," *Expert Opin. Drug Saf.*, 4(6):1-9 (2005).
Kelly et al., "Fecal Microbiota Transplant for Treatment of Clostridium difficile Infection in Immunocompromised Patients," *Am J Gastroenterol*, 109:1065-1071 (2014).

(56) References Cited

OTHER PUBLICATIONS

Kobashi et al., "Metabolism of Sennosides by Human Intestinal Bacteria," *Journal of Medicinal Plant Research*, 40(3):225-236 (1980).
Leis et al., "Fecal microbiota transplantation: A 'How-To' guide for nurses," *Collegian*, 22:445-451 (2015).
Lin et al., "Twelve Week Storage Trial of Microbial Viability in Lyophilized and Frozen Fecal Microbiota Preparations," Poster Presentation—Digestive Disease Week 2015, Washington, D.C. USA.
Paramsothy et al., "Gastroenterologist perceptions of faecal microbiota transplantation," *World J Gastroenterol*, 21(38): 10907-10914 (2015).
Pearce et al., "Modification of the colonic microflora using probiotics: The way forward?," *Gut*, 41(Suppl 3):A63 (1997).
Pearce et al., "The use of probiotic therapy as a novel approach to the management of irritable bowel syndrome: a preliminary study," *J Gastroenterol & Hepatol*, 12(Suppl):A129 (1997).
Wettstein et al., "Skewered diverticulum: another cause of abdominal pain," *Internal Med J*, 31(8):495-496 (2001).
Khanna et al., "A Novel Microbiome Therapeutic Increases Gut Microbial Diversity and Prevents Recurrent Clostridium difficile Infection," *The Journal of Infectious Diseases*, 214:173-81 (2016).
"Autoimmune Disease List," *American Autoimmune Related Diseases Association*, pp. 1-4 (2017) <https://www.aarda.org/diseaselist/>.
"Certain infectious and parasitic diseases (A00-B99)," *International Statistical Classification of Diseases and Related Health Problems*, 10th Revision (ICD-10)—WHO Version, Chapter 1, pp. 1 (2016) <www.apps.who.int/classifications/icd10/browse/2016/eng/I>.
"Spore-Forming Gram-Positive Bacilli: *Bacillus* and *Clostridium* Species," *Jawetz, Melnick, & Adelberg's Medical Microbiology*, 26th Edition, Chapter 11, pp. 1-15 (2012).
"Functional Anatomy of Prokaryotic and Eukaryotic Cells," printed Mar. 16, 2017 <http://classes.midlandstech.edu/carterp/courses/bio225/chap04/lecture2.htm>.
Abrams, "Open-Label, Uncontrolled Trial of Bowel Sterilization and Repopulation with Normal Bowel Flora for Treatment of Inflammatory Bowel Disease," *Current Therapeutic Research*, 58(12):1001-1012 (1997).
Anderson et al., "Systematic review: faecal microbiota transplantation in the management of inflammatory bowel disease," *Aliment. Pharmacol. Ther.*, 36:503-16 (2012).
Andoh et al., "Terminal restriction fragment polymorphisum analyses of fecal microbiota in five siblings including two with ulcerative colitis," *Journal of Clinical Gastroenterology*, 2:343-345 (2009).
Aroniadis et al., "Intestinal Microbiota and the Efficacy of Fecal Microbiota Transplantation in Gastrointestinal Disease," Gastroenterology and Hepatology, 10(4): 230-7 (2014).
Atarashi et al., "Induction of Colonic Regulatory T Cells by Indigenous *Clostridium* Species," *Science*, 331(6015):337-341, published online Dec. 23, 2010.
Atarashi et al., "$T_{reg}$ induction by a rationally selected mixture of *Clostridia* strains from the human microbiota," *Nature*, 500(7461):232-236 (2013).
Atarashi et al., "WS/PP-064-03 Regulation of colonic regulatory T cells by *Clostridium* species," *International Immunology*, 22(Suppl 1, Part 3), pp. 1-3 (2010).
Atarashi et al., WS-064 Mucosal immunity: homeostasis, 14th ICIC Abstract book, 14th International Congress of Immunology, pp. iii131-iii133 (2010).
Belkaid et al., "Natural regulatory T cells in infectious disease," *Nature Immunology*, 6(4):353-360 (2005).
Bolte, "Therapies for Gastrointestinal and Neurological Disorders," U.S. Appl. No. 60/214,813, filed Jun. 28, 2000.
Brandt et al., "Long-Term Follow-Up Study of Fecal Microbiota Transplantation (FMT) for Ulcerative Colitis (UC)," Am. J. Gastroenterol., 107(Suppl 1:S657 (2012).
Browne et al., "Culturing of 'unculturable' human microbiota reveals novel taxa and extensive sporulation," *Nature*, 533(7604):543-546 (2016).
Bueche et al., "Quantification of Endospore-Forming *Firmicutes* by Quantitative PCR with the Functional Gene spo0A," *Applied and Environmental Microbiology*, 79(17):5302-5312 (2013).
Cammorata et al., "Review article: biofile formation by Helicobacter pylori as a target for eradication of resistant infection," Aliment Pharmacol Ther, 36:222-30 (2012).
Cato et al., "*Clostridium oroticum* comb. nov. amended description," *International Journal of Systematic Bacteriology*, 17(1):9-13 (1968).
Celik et al., "Factors influencing the stability of freeze-dried stress-resilient and stress-sensitive strains of bifidobacteria," J. Dairy Sci., 96(6):3506-16 (2013).
Cherif et al., "Thuricin 7: a novel bacteriocin produced by Bacillus thuringiensis BMG1.7, a new strain isolated from soil," Letters in Applied Microbiology, 32:243-7 (2001).
Choi et al., "Fecal Microbiota Transplantation: Current Applications, Effectiveness, and Future Perspectives," Clin. Endosc., 49:257-265 (2016).
Chu et al., "Profiling Living Bacteria Informs Preparation of Fecal Microbiota Transplantations," *PLOS One*, 1-16 (2017).
Collins et al., "The Phylogeny of the Genus *Clostridium*: Proposal of Five New Genera and Eleven New Species Combinations," *International Journal of Systematic Bacteriology*, pp. 812-826 (1994).
De Giulio et al., "Use of Algiinate and Cryo-Protective Sugars to Improve the Viability of Lactic Acid Bacteria After Freezing and Freeze-Drying," World Journal of Microbiology & Biotechnology, 21:739-746 (2005).
Dewhirst et al., "Phylogeny of the Defind Murine Microbiota: Altered Schaedler Flora," *Applied and Environmental Microbiology*, 65(8):3287-3292 (1999).
Extended European Search Report dated Nov. 30, 2016, in European Patent Application No. 16193790.9.
Frank et al., "Molecular-phylogenetic characterization of microbial community imbalances in human inflammatory bowel diseases," *PNAS*, 104(34):13780-13785 (2007).
Gaboriau-Routhiau et al., "The Key Role of Segmented Filamentous Bacteria in the Coordinated Maturation of Gut Helper T Cell Responses," *Immunity*, 31(4):677-689 (2009).
Geuking et al., "Intestinal Bacterial Colonization Induces Mutualistic Regulatory T Cell Respones," *Immunity*, 34:794-806 (2011).
Gustafsson et al., "The Effect of Faecal Enema on Five Microflora-Associated Characteristics in Patients with Antibiotic-Associated Diarrhoea," Scandinavian Journal of Gastroenterology, 34:580-586 (1999).
Hayashi et al., "Phylogenetic Analysis of the Human Gut Microbiota Using 16S rDNA Clone Libraries and Strictly Anaerobic Culture-Based Methods," *Microbiol. Immunol.*, 46(8):535-548 (2002).
Hecker et al., "Fecal Microbiota Transplantation by Freeze-Dried Oral Capsules for Recurrent Clostridium difficile Infection," Open Forum Infect Dis, 3(2): 1-2 (2016).
Honda et al., "Regulation of T Cell Responses by Intestinal Commensal Bacteria," *Journal of Intestinal Microbiology*, vol. 25, 2nd Edition:104 (2011).
Immunology in the 21st Century: Defeating Infection, Autoimmunity, Allergy, and Cancer, ICI 2010 Wrap-up Report, 14th International Congress of Immunology, pp. 1 (2010).
International Search Report and Written Opinion dated Aug. 8, 2016, in International Application No. PCT/US2016/032695, 10 pgs.
Itoh et al., "Characterization of clostridia isolated from faeces of limited flora mice and their effect on caecal size when associated with germ-free mice," *Laboratory Animals*, 19:111-118 (1985).
Itoh et al., "Intestinal bacteria antagonistic to *Clostridium difficile*in mice," *Laboratory Animals*, 21:20-25 (1987).
Ivanov et al., "Specific Microbiota Direct the Differentiation of IL-17-Producing T-Helper Cells in the Mucosa of the Small Intestine," *Cell Host & Microbe*, 4:337-349 (2008).

(56) References Cited

OTHER PUBLICATIONS

Jacob et al., "Single Delivery of High-Diversity Fecal Microbiota Preparation by Colonoscopy is Safe and Effective in Increasing Microbial Diversity in Active Ulcerative Colitis," *Inflamin Bowel Dis.*, 0(0):1-9 (2017).
Janeway et al., "Adaptive Immunity to Infection," *Immunobiology*, 6th Edition, Chapter 10, pp. 414 (2005).
Janeway, Jr. et al., "Autoimmune responses are directed against self antigens," Immunobiology: *The Immune System in Health and Disease*, 5th Edition, pp. 1-4 (2001).
Kageyama et al., "Phylogenetic and phenotypic evidence for the transfer of Eubacterium aerofaciens to the genus *Collinsella* as *Collinsella aerofaciens* gen. nov., comb. nov.," International Journal of Systematic Bacteriology, 49:557-565 (1999).
Kakihana et al., "Fecal microbiota transplantation for patients with steriod-resistant acute graft-versus-host disease of the gut," *Blood*, 128(16):2083-2088 (2016).
Kang et al., "Microbiota Transfer Therapy alters gut ecosystem and improves gastrointestinal and autism symptoms: an open-label study," Microbiome, 5:10, 16 pages (2017).
Kelly et al., "Commensal gut bacteria: mechanisms of immune modulation," *TRENDS in Immunology*, 26(6):326-333 (2005).
Keynan et al., "The Role of Regulatory T Cells in Chronic and Acute Viral Infections," *Clinical Infectious Diseases*, 46:1046-1052 (2008).
Klaenhammer, "Bacteriocins of lactic acid bacteria," Biochimie, 70:337-49 (1988).
Koch, "What size should a bacterium be? A question of scale," Annu. Rev. Microbiol., 50:317-48 (1996).
Krogius-Kurikka et al., "Sequence analysis of percent G+C fraction libraries of human faecal bacterial DNA reveals a high number of *Antinobacteria,*" BMC Microbiology, 9(68):1-13 (2009).
Kunde et al.,"Safety , Tolerability, and Clinical Response After Fecal Transplantation in Children and Young Adults With Ulcerative Colitis," *JPNG*, 56(6):597-601 (2013).
Larsen et al., "Gut Microbiota in Human Adults with Type 2 Diabetes Differs from Non-Diabetic Adults," PLoS ONE, 5(2): e9085-e9095 (2010).
Lau et al., "Bacteraemia caused by Anaerotruncus colihominisand emended description of the species," *J Clin Pathol*, 59:748-752 (2006).
Lawson et al.,"*Anaerotruncus colihominis* gen. nov., sp. nov., from human faeces," *International Journal of Systematic and Evoluntionary Microbiology*, 54:413-417 (2004).
Lawson et al., "Anaerotruncus," *Bergey's Manual of Systematics of Archae and Bacteria*, pp. 1-4 (2009).
Louis et al., "Diversity, metabolism and microbial ecology of butyrate-producing bacteria from the human large intestine," *FEMS Microbiology Letters*, 294:1-8 (2009).
Ludwig et al., "Taxonomic outline of the phylum Firmicutes," Bergey's Manual of Systematic Bacteriology, 3:15-17 (2009).
Maizels et al., "Regulatory T cells in Infection," *Advances in Immunology*, Chapter 3, 112:73-136 (2011).
Martin-Dejardin et al., "A way to follow the viability of encapsulated Bifidobacterium bifidum subjected to a freeze-drying process in order to target the colon: Interest of flow cytometry," European Journal of Pharmaceutical Sciences, 49:166-74 (2013).
Moayyedi et al., "Fecal Microbiota Transplantation Induces Remission in Patients With Active Ulcerative Colitis in a Randomized Controlled Trial," Gastroenterology, 149(1):102-9 (2015).
Momose et al.,"16S rRNA gene sequence-based analysis of clostridia related to conversion of germfree mice to the normal state," *Journal of Applied Microbiology*, 107:2088-2097 (2009).
Niu et al., "Prevalence and Impact of Bacteriophages on the Presence of *Escherichia coli* O157:H7 in Feedlot Cattle and Their Environment," Applied and Environmental Microbiology, 75(5): 1271-8 (2009).
Office Action dated Sep. 18, 2015, in European Patent Application No. 11 728 077.6.

O'Garra et al., "IL-10—producing and naturally occuring CD4+ Tregs: limiting collateral damage," *The Journal of Clinical Investigation*, 114:1372-1378 (2004).
Okada et al., "Effects of Fecal Microorganisms and Their Chloroform-Resistant Variants Derived from Mice, Rats, and Humans on Immunological and Physiological Characteristics of the Intestines of Ex-germfree Mice," *Infection and Immunity*, 62(12):5442-5446 (1994).
Ott et al., "Efficacy of Sterile Fecal Filtrate Transfer for Treating Patients With Clostridium difficile Infection," Gastroenterology, 152(4):799-811 (2017).
Paramsothy et al., "Multidonor intensive faecal microbiota transplantation for active ulcerative colitis: a randomised placebo-controlled trial," The Lancet, published online, 11 pages (2017).
Qiu et al., "*Faecalibacterium prausnitzii* upregulates regulatory T cells and anti-inflammatory cytokines in treating TNBS-induced colitis," *Journal of Crohn's and Colitis*, 7:e558-e568 (2013).
Ramesh et al., "Prevention of Clostridium difficile-induced ileocecitis with Bacteriophage," *Anaerobe*, 5:69-78 (1999).
Response to Office Action filed Feb. 25, 2014, in European Patent Application No. 11 728 077.6.
Response to Office Action filed Jan. 28, 2015, in European Patent Application 11 728 077.6.
Response to Office Action filed Nov. 18, 2015, in European Patent Application No. 11 728 077.6.
Roberts, Generation and Development Microbial Drug Products, CSO Vedanta Biosciences, 1st Microbiome Drug Development Summit, pp. 1-17 (2016).
Rossen et al., "Findings From a Randomized Controlled Trial of Fecal Transplantation for Patients with Ulcerative Colitis," Gastroenterology, 149(1):110-8 (2015).
Sanchez et al., "The Role of Natural Regulatory T cells in Infection," *Immunol Res.*, 49(0):124-134 (2011).
Sartor, "Therapeutic correction of bacterial dysbiosis discovered by molecular techniques," *PNAS*, 105(43):16413-16414 (2008).
Sghir et al., "Quantification of Bacterial Groups within Human Fecal Flora by Oligonucleotide Prode Hybridization," *Applied and Environmental Microbiology*, 66(5):2263-2266 (2000).
Sokol et al., *Faecalibacterium prausnitzii* is an anti-inflammatory commensal bacterium identified by gut microbiota analysis of Crohn disease patients, *Proceedings of the National Academy of Sciences*, 105(43):16731-16736 (2008).
Sokol et al., "Low Counts of *Faecalibacterium prausnitzii* in Colitis Microbiota," *Inflamm. Bowel Dis.*, pp. 1-7 (2009).
Sunil et al., "Design and evaluation of lornoxicam bilayered tablets for biphasic release," Brazilian Journal of Pharmaceutical Sciences, 48(4):609-19 (2012).
Takaishi et al., "Imbalance in intestinal microflora constitution could be involved in the pathogenesis of inflammatory bowel disease," *J. Med. Microbial.*, 298:463-472 (2008).
Van Andel et al., "Interleukin-12 Has a Role in Mediating Resistance of Murine Strains to Tyzzer's Disease," Infect. Immun., 66(10):4942-4946 (1998).
Van Immerseel et al., "Butyric acid-producing anaerobic bacteria as a novel probiotic treatment approach for inflammatory bowel disease," *Journal of Medical Microbiology*, 59:141-143 (2010).
Vulevic et al., "Modulation of the fecal microflora profile and immune function by a novel trans-galactooligosaccharide mixture (B-GOS) in healthy elderly volunteers," Am J Clin Nutr, 88:1438-46 (2008).
Wachsmann et al. ,"Characterization of an Orotic Acid Fermenting Bacterium, Zymobacteriutn oroticum, nov. gen., nov. spec.," *Journal of Bacteriology*, 68(4):400-404 (1954).
Warren et al., "*Clostridium aldenense* sp. nov. and *Clostridium citroniae* sp. nov. Isolated from Human Clinical Infections," *Journal of Clinical Microbiology*, 44(7):2416-2422.
Weingarden et al., "Dynamic changes in short- and long-term bacterial composition following fecal microbiota transplantation for recurrent Clostridium difficile infection," Microbiome, 3(10), 8 pages (2015).

(56) References Cited

OTHER PUBLICATIONS

Wells et al., "Clostridia: Sporeforming Anaerobic Bacilli," *Medical Microbiology—NCBI Bookshelf*, 4th Edition, Chapter 18, pp. 1-20 (1996) <https://www.ncbi.nlm.nih.gov/books/NBK8219/?report=printable>.
Zhou et al., "Total fecal microbiota transplantation alleviates high-fat diet-induced steatohepatitis in mice via beneficial regulation of gut microbiota," *Scientific Reports (Nature)*, 7(1529):1-11 (2017).
"ARGF—'Autologous Rehabilitation of Gastrointestinal Flora,'" *Medipex Report for Medilink NW*, pp. 1-42, n.d., Web, Feb. 10, 2012 <http://www.bacteriotherapy.org/docs/medipex-report.pdf>.
"Frequently Asked Questions about *Clostridium difficile* for Healthcare Providers," Healthcare-associated Infections (HAIs), *Centers for Disease Control and Prevention*, pp. 1-6, Nov. 25, 2010, updated Mar. 6, 2012, Web, May 19, 2014 <http://www.cdc.gov/HAI/organisms/cdiff/Cdiff_faqs_HCP.html>.
"Monilia," Def. 1, *Stedman's Medical Dictionary*, n.d., Web, Nov. 22, 2005.
"Probiotic," Def. 1, MSN Encarta—Dictionary, Encarta, n.d., Web, Dec. 1, 2005.
Aas et al., "Recurrent *Clostridium difficile* Colitis: Case Series Involving 18 Patients Treated with Donor Stool Administered via a Nasogastric Tube," *Clinical Infectious Diseases*, 36(5):580-585 (2003).
Acha et al., "Changes of viability and composition of the *Escherichia coli* flora in faecal samples during long time storage," *Journal of Microbiological Methods, Elsevier*, 63(3):229-238 (2005).
Al-Eidan et al., "*Clostridium difficile*-associated diarrhoea in hospitalised patients," *J Clin. Pharm. Ther.*, 25(2):101-109 (2000).
Al-Nassir et al., "Comparison of Clinical and Microbiological Response to Treatment of *Clostridium difficile*-Associated Disease with Metronidazole and Vancomycin," *Clin Infect Dis.*, 47(1):56-62 (2008).
Anand et al., "Epidemiology, clinical manifestations, and outcome of *Clostridium difficile*-associated diarrhea," *Am J Gastroenterol.*, 89(4):519-23 (1994).
Ananthakrishnan et al., "Excess hospitalisation burden associated with *Clostridium difficile* in patients with inflammatory bowel disease," *Gut*, 57(2):205-210 (2007).
Andrews et al., "'Putting back the bugs': Bacterial Treatment Relieves Chronic Constipation and Symptoms of Irritable Bowel Syndrome," *Med. J Aust.*, 159(9):633-634 (1993).
Anorexia nervosa, Encyclopedia Index A, healthAtoZ, Medical Network, Inc., pp. 1-7, n.d., Web, Nov. 23, 2005 <http://www.healthatoz.com/healthatoz/Atoz/ency/anorexia_nervosa.jsp>.
Arkkila et al., "Fecal Bacteriotherapy for Recurrent *Clostridium difficile* Infection," *Gastroenterology*, 138(5): S1-S5 (2010).
Autism, Health Encyclopedia—Diseases and Conditions, *The Health Scout Network*, pp. 1-5, n.d., Web, Nov. 22, 2005 <www.healthscout.com>.
Autism, Treatment, Prognosis, Healthcommunities.com, Inc., pp. 1-4, n.d., Web. Jan. 28, 2009 <http://www.neurologychannel.com/common/PrintPage.php>.
Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print& DSECTION=all>.
Backhed et al., "Host-bacterial mutualism in the human intestine," *Science*, 307(5717):1915-1920 (2005).
Backhed et al., "Mechanisms underlying the resistance to diet-induced obesity in germ-free mice," *PNAS USA*, 104(3):979-984 (2007).
Backhed et al., "The gut microbiota as an environmental factor that regulates fat storage," *PNAS USA*, 101(44):15718-15723 (2004).
Bakken et al., "Fecal bacteriotherapy for recurrent *Clostridium difficile* infection," *Anaerobe*, 15(6):285-289 (2009).
Bakken et al., "Treating *Clostridium difficile* Infection with Fecal Microbiota Transplantation," *Clinical Gastroenterology and Hepatology*, 9(12):1044-1049 (2011).

Bartlett et al., "Clinical recognition and diagnosis of *Clostridium difficile* infection," *Clin Infect Dis.*, 46(Suppl 1): S12-S18 (2008).
Bartlett, "*Clostridium difficile*-associated Enteric Disease," *Curr Infect Dis Rep.*, 4(6):477-483 (2002).
Bengmark et al., "Bioecological control of inflammatory bowel disease," *Clinical Nutrition*, 26(2): 169-181 (2007).
Bennet et al., "Treatment of ulcerative colitis by implantation of normal colonic flora," *Lancet*, 333(8630):164 (1989).
Benson et al., "Changing epidemiology of *Clostridium difficile*-associated disease in children," *Infect Control Hosp Epidemiol.*, 28(11):1233-1235 (2007).
Blaser et al., "What are the consequences of the disappearing human microbiota?" *Nat. Rev. Microbiol.*, 7(12):887-894 (2009).
Blaser, "Who are we? Indigenous microbes and the ecology of human diseases," *EMBO Rep*, 7(10):956-960 (2006).
Bolte, "Autism and *Clostridium tetani*," *Medical Hypotheses*, 51(2): 133-144 (1998).
Borody et al., "Bacteriotherapy Using Fecal Flora: toying with human motions," *J. Clin. Gastroenterol.*, 38(6):475-483 (2004).
Borody et al., "Bowel-flora alteration: a potential cure for inflammatory bowel disease and irritable bowel syndrome?" *Med. J. Aust.*, 150:604 (1989).
Borody et al., "Fecal microbiota transplantation and emerging applications," *Nat. Rev. Gastroenterol. Hepatol.*, 9(2):88-96 (2011).
Borody et al., "Fecal microbiota transplantation: current status and future directions," *Expert Review of Gastroenterology & Hepatology*, 5(6):653-655 (2011).
Borody et al., "Treatment of ulcerative colitis using fecal bacteriotherapy," *J. Clin. Gastroenterol.*, 37(1):42-47 (2003).
Borriello, "Clostridial Disease of the Gut," *Clinical Infectious Diseases, The University of Chicago*, 20(Suppl 2): S242-S250 (1995).
Bowden et al., "Pseudomembraneous enterocolitis: mechanism for restoring floral homeostasis," *Am Surg.*, 47(4):178-183 (1981).
Brandt et al., "Endoscopic Fecal Microbiota Transplantation: 'First-Line' Treatment for Severe *Clostridium difficile* Infection?" *J. Clin. Gastroenterol.*, 45(8):655-657 (2011).
Brandt et al., "Fecal microbiota transplantation for recurrent *Clostridium difficile* infection," *J Clin Gastroenterol.*, 45( Suppl): S159-S167 (2011).
Cano et al., "Revival and identification of bacterial spores in 25-40 million year old Dominican Amber Science," *Science*, 268(5213):1060-1064 (1995).
Center for Disease Control, "Severe *Clostridium difficile*-associated disease in populations previously at low risk—four states, 2005." *Morbidity and Mortality Weekly Report*, 54(47):1201-1205 (2005).
Chang et al., "Decreased diversity of the fecal Microbiome in recurrent *Clostridium difficile*-associated diarrhea," *J. Infect. Dis.*, 197(3):435-438 (2008).
Chen et al., "A mouse model of *Clostridium difficile*-associated disease," *Gastroenterology*, 135(6):1984-1992 (2008).
Chopra et al., "Recent epidemiology of *Clostridium difficile* infection during hematopoietic stem cell transplantation," *Clin Transplant*, 25(1):E82-E87 (2011).
Citron et al., "In Vitro Activities of CB-183,315, Vancomycin, and Metronidazole against 556 Strains of *Clostridium difficile*, 445 Other Intestinal Anaerobes, and 56 *Enterobacteriaceae* Species," *Antimicrob Agents Chemother.*, 56(3):1613-1615 (2012).
Claesson et al., "Comparison of two next-generation sequencing technologies for resolving highly complex microbiota composition using tandem variable 16S rRNA gene regions," *Nucleic Acids Research*, 38(22):1-13 (2010).
Claus et al., "Colonization-induced host-gut microbial metabolic interaction," *MBio*, 2(2): e 00271-00210 (2011).
Claus et al., "Systemic multicompartmental effects of the gut microbiome on mouse metabolic phenotypes," *Mol. Syst. Biol.*, 4(1):219 (2008).
Cohen et al., "Clinical practice guidelines for *Clostridium difficile* infection in adults: 2010 update by the society for healthcare epidemiology of America (SHEA) and the infectious diseases society of America (IDSA)," *Infect Control Hosp Epidemiol.*, 31(5):431-55 (2010).

(56) References Cited

OTHER PUBLICATIONS

Crohn's Disease, Prevention, Health Guide A-Z, WebMDHealth, pp. 1-2, n.d., Web, Oct. 23, 2005 <http://mywebmd.com/hw/inflammatory.sub.--bowel/uf6012.asp>.
Crowther, "Transport and Storage of Faeces for Bacteriological Examination," *Journal of Applied Bacteriology*, 34(2):477-483 (1971).
Cutolo et al., "Fecal feedings as a therapy in *Staphylococcus enterocolitis*," *NY State J Med*, 59:3831-3833 (1959).
Dale et al., "Molecular interactions between bacterial symbionts and their hosts," *Cell*, 126(3):453-465 (2006).
Dan et al., "Comparison of preservation media and freezing conditions for storage of specimens of faeces," *J. Med Microbiology*, 28:151-154 (1989).
Defang et al., "In vitro and in vivo evaluation of two extended Release preparations of combination metformin and glipizide:" *Drug Develop. & Indust. Pharm.*, 31:677-685 (2005).
Dendukuri et al., "Probiotic therapy for the prevention and treatment of *Clostridium difficile*-associated diarrhea: a systematic review," *CMAJ*, 173(2):167-170 (2005).
Derwent Abstract Accession No. 98-230427/20, WO 98/13068 A, (Kuperman VB) Apr. 2, 1998.
Dethlefsen et al., "An ecological and evolutionary perspective on human-microbe mutualism and disease," *Nature*, 449(7164):811-818 (2007).
DuPont, "The search for effective treatment of *Clostridium difficile* infection," N Engl J Med., 364(5):473-475 (2011).
Eckburg et al., "Diversity of the human intestinal microbial flora," *Science*, 308(5728):1635-1638 (2005).
Eiseman et al., "Fecal enema as an adjunct in the treatment of pseudomembranous enterocolitis," *Surgery*, 44(5):854-859 (1958).
Extended European Search Report dated Apr. 3, 2014, in European Patent Application No. 11813951.8.
Faust et al., "Treatment of recurrent pseudomembranous colitis (RPMC) with stool transplantation (ST): Report of six (6) cases," *Can J Gastroenterol.*, 16:A43 (2002).
Fenton et al., "Pseudomembranous colitis associated with antibiotic therapy—an emerging entity," Can Med Assoc J., 111(10):1110-1111 (1974).
Floch et al., "Probiotics and Dietary Fiber, The Clinical Coming of Age of Intestinal Microecology," *J. Clin. Gastroenterology*, 27(2):99-100 (1998).
Floch, "Fecal Bacteriotherapy, Fecal Transplant, and the Microbiome," *J. Clin. Gastroenterol.*, 44(8):529-530 (2010).
Flotterod et al., "Refractory *Clostridium difficile* infection. Untraditional treatment of antibiotic-induced colitis," *Tidsskr nor Laegeforen*, 111:1364-1365 (1991).
Frantzen et al., "Empirical evaluation of preservation methods for faecal DNA," *Molecular Ecology*, 7(10):1423-1428 (1998).
Freeman et al., "The changing epidemiology of *Clostridium difficile* infections," *Clin Microbiol. Rev.*, 23(3):529-549 (2010).
Frese et al., "The evolution of host specialization in the vertebrate gut symbiont Lactobacillus reuteri," *PloS Genet.*, 7(2):e1001314 (2011).
Garborg et al., "Results of faecal donor instillation therapy for recurrent *Clostridium difficile*-associated diarrhoea," *Scand J Infect Dis.*, 42(11-12):857-61 (2010).
Garey et al., "Meta-analysis to assess risk factors for recurrent *Clostridium difficile* infection," *J Hosp. Infect.*, 70(4):298-304 (2008).
Gerding, "Management of *Clostridium difficile* infection: thinking inside and outside the box," *Clin Infect Dis.*, 51(11):1306-13 (2010).
Gough et al., "Systematic review of intestinal microbiota transplantation (fecal bacteriotherapy) for recurrent *Clostridium difficile* infection," *Clin. Infect. Dis.*, 53(10):994-1002 (2011).
Grehan et al., "Durable alteration of the colonic microbiota by the administration of donor fecal flora," *Journal of Clinical Gastroenterology*, 44(8):551-561 (2010).
Guarner et al., "Gut flora in health and disease," *Lancet*, 361(9356):512-519 (2003).
Gustafsson et al., "Faecal Short-Chain Fatty Acids in Patients with Antibiotic-Associated Diarrhoea, before and after Faecal Enema Treatment," *Scand J Gastroenterol*, 33:721-727 (1998).
Hamilton et al., "Change in microbial community composition of in patients with recalcitrant *Clostridium difficile* colitis treated with fecal bacteriotherapy," International Human Microbiome Congress, Poster and Presentation, Vancouver, ON, Canada, Mar. 9-11, 2011.
Hamilton et al., "High-throughput DNA sequence analysis reveals stable engraftment of gut microbiota following transplantation of gut microbiota following transplantation of previously frozen fecal bacteria," *Gut Microbes*, 4(2):1-11 (2013).
Hamilton et al., "Standardized Frozen Preparation for Transplantation of Fecal Microbiota for Recurrent *Clostridium difficile* Infection," Article and Supplementary Material, *Am. J. Gastroenterol.*, 107(5):761-767 (2012).
Hellemans et al., "Fecal transplantation for recurrent *Clostridium difficile* colitis, an underused treatment modality," *Acta Gastroenterol Belg.*, 72(2):269-70 (2009).
Hensel et al., "Vagal Ascent and Distribution of 125 I-Tetanus Toxin after Injection into the Anterior Wall of the Stomach," *Naunyn-Schmiedeberg's Arch. Pharmacol*, 276:395-402 (1973).
Hooper et al., "How host-microbial interactions shape the nutrient environment of the mammalian intestine," *Annu. Rev. Nutr.*, 22:283-307 (2002).
Hope et al., "Sporadic colorectal cancer-role of the commensal microbtota," *FEMS Microbiol. Lett.*, 244:1-7 (2005).
Hota et al., "Determining Mortality Rates Attributable to *Clostridium difficile* Infection," *Emerg. Infect. Dis.*, 18(2):305-307 (2012).
Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.
Hu et al., "Prospective derivation and validation of a clinical prediction rule for recurrent *Clostridium difficile* infection," *Gastroenterology*, 136:1206-1214 (2009).
Huang et al., "Once-daily propranolol extended-release tablet dosage form: formulation design and in vitro/in vivo investigation," *European J. of Pharm. & Biopharm.*, 58:607-614 (2004).
Huttenhower et al., "Structure, function and diversity of the healthy human microbiome," The Human Microbiome Project Consortium, *Nature*, 486:207-214 (2012).
Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowels/chrohns.html>.
International Preliminary Examination Report completed Nov. 19, 2002, in International Application No. PCT/AU2001/000907, 19 pgs..
International Preliminary Report on Patentability completed Dec. 12, 2012, in International No. PCT/AU2011/000987, 35 pgs.
International Preliminary Report on Patentability completed Mar. 12, 2015, in International Application No. PCT/AU2013/001362, 29 pgs.
International Preliminary Report on Patentability dated Sep. 10, 2013, in International Application No. PCT/US2012/028484, 10 pgs.
International Search Report and Written Opinion dated Feb. 5, 2014, in International Application No. PCT/AU2013/001362, 17 pgs.
International Search Report and Written Opinion dated Jul. 31, 2014, in International Application No. PCT/US2014/027391, 16 pgs.
International Search Report and Written Opinion dated Oct. 28, 2011, in International No. PCT/AU2011/000987, 18 pgs.
International Search Report dated Aug. 10, 2012, in International Application No. PCT/US2012/028484, 7 pgs.
International Search Report dated Jul. 29, 2014, in International Application No. PCT/AU2014/000478, 7 pgs.
Irrgang et al., "The historical Development of Mutaflor therapy," Ardeypharm GmbH, pp. 1-38 (1988) <http://www.ardeypharm.de/pdfs/en/mutaflor_historical_e.pdf? >.

(56) References Cited

OTHER PUBLICATIONS

Irritable Bowel Syndrome (IBS), Health A to Z. InteliHealth, pp. 1-4, n.d., Web, Oct. 23, 2005 <http://www.intelihealth.com>.
Issa et al., "*Clostridium difficile* and Inflammatory Bowel Disease," *Inflamm Bowel Dis.*, 14(10):1432-1442 (2008).
Issa et al., "Impact of *Clostridium difficile* on inflammatory bowel disease," *Clin. Gastroenterol. Hepatol.*, 5(3):345-351 (2007).
Jarvis et al., "National point prevalence of *Clostridium difficile* in US health care facility inpatients, 2008," *Am. J. Infect. Control*, 37:263-270 (2009).
Johnson et al., "Interruption of Recurrent *Clostridium difficile*-Associated Diarrhea Episodes by Serial Therapy with Vancomycin and Rifaximin," *Clin. Infect. Dis.*, 44(6):846-848 (2007).
Johnson et al., "Rifaximin Redux: Treatment of recurrent *Clostridium difficile* infections with Rifaximin immediately post-vancomycin treatment," *Anaerobe*, 15(6):290-291 (2009).
Jorup-Ronstrom et al., ["Feces culture successful therapy in *Clostridium difficile* diarrhea"], *Lakartidningen*, 103(46):3603-3605 (2006).
Kageyama et al., "Emendation of genus *Collinsella* and proposal of *Collinsella stercoris* sp. nov. and *Collinsella intestinalis* sp. nov.," *International Journal of Systematic and Evolutionary Microbiology*, 50:1767-1774 (2000).
Kamboj et al., "Relapse versus reinfection: surveillance of *Clostridium difficile* infection," *Clin Infect Dis.*, 53(10):1003-1006 (2011).
Karas et al., "A review of mortality due to *Clostridium difficile* infection," *J Infect.*, 61(1):1-8 (2010).
Kassam et al., "Fecal transplant via retention enema for refractory or recurrent *Clostridium difficile* infection," *Arch Intern Med.*, 172(2):191-193 (2012).
Kelly et al., "*Clostridium difficile* —more difficult than ever," *N Engl J Med*, 359(18):1932-1940 (2008).
Kelly et al., "*Clostridium difficile* colitis," *N Engl J Med*, 330(4):257-62 (1994).
Kelly et al., "Fecal microbiota transplantation for relapsing *Clostridium difficile* infection in 26 patients: methodology and results," *J. Clin. Gastroenterol.*, 46(2):145-149 (2012).
Khanna et al., "The epidemiology of community-acquired *Clostridium difficile* infection: a population-based study," *Am J Gastroenterol.*, 107(1):89-95 (2012).
Khanna et al., "The growing incidence and severity of *Clostridium difficile* infection in inpatient and outpatient settings," *Expert Rev Gastroenterol Hepatol.*, 4(4):409-16 (2010).
Kharidia et al., "The Activity of a Small Lytic Peptide PTP-7 on *Staphylococcus aureus* Biofilms," *J. Microbiol.*, 49(4):663-668 (2011).
Khoruts et al., "Changes in the composition of the human fecal microbiome after bacteriotherapy for recurrent *Clostridium difficile*-associated diarrhea," *J. Clin. Gastroenterol.*, 44(5):354-360 (2010).
Khoruts et al., "Therapeutic transplantation of the distal gut microbiota," *Mucosal Immunol.*, 4(1):4-7 (2011).
Kim et al., "Effect of Rifampin on the Plasma Concentration and the Clinical Effect of Haloperidol Concomitantly Administered to Schizophrenic Patients," *Journal of Clinical Psychopharmacology*, 16(3):247-252 (1996).
Kim et al., "In Vitro Culture Conditions for Maintaining a Complex Population of Human Gastrointestinal Tract Microbiota," *Journal of Biomedicine and Biotechnology*, 2011(Article ID 838040):1-10 (2011) <http://www.hindawi.com/journals/bmri/2011/838040/>.
Kleiman et al., "Comparison of two coprological methods for the veterinary diagnosis of fasciolosis," *Arquivo Brasileiro de Medicina Veterinária e Zootécnica*, 55(2):181-185 (2005).
Kuijper et al. "Update of *Clostridium difficile* Infection due to PCR Ribotype 027 in Europe, 2008," *Euro. Surveill.*, 13(31):Article 5 (2008).

Kuksal et al., "Formulation and In Vitro, In Vivo Evaluation of Extended- release Matrix Tablet of Zidovudine: Influence of Combination of Hydrophilic and Hydrophobic Matrix Formers," *AAPS Pharm.*, 7(1):E1-E9 (2006).
Kyne et al., "Association between antibody response to toxin a and protection against recurrent *Clostridium difficile* diarrhea," *Lancet*, 357(9251):189-93 (2001).
Kyne et al., "Asymptomatic carriage of *Clostridium difficile* and serum levels of IgG antibody against toxin A," *N Engl J Med.*, 342(6):390-397 (2000).
Kyne et al., "Factors associated with prolonged symptoms and severe disease due to *Clostridium difficile*," *Age and Ageing*, 28(2):107-13 (1999).
Kysela et al., "Serial analysis of V6 ribosomal sequence tags (SARST-V6): a method for efficient, high-throughput analysis of microbial community composition," *Environmental Microbiology*, 7(3):356-364 (2005).
Labbé et al., "*Clostridium difficile* infections in a Canadian tertiary care hospital before and during a regional epidemic associated with the BI/NAP1/027 strain," *Antimicrob Agents Chemother.*, 52(9):3180-7 (2008).
Lamontagne et al., "Impact of emergency colectomy on survival of patients with fulminant *Clostridium difficile* colitis during an epidemic caused by a hypervirulent strain," *Ann. Surg.*, 245(2):267-272 (2007).
Lee, "A Prospective Randomized Multi-Centre Trial of Fresh vs. Frozen-and-Thawed Human Biotherapy (Fecal Transplant) for Recurrent *Clostridium difficile* Infection," *U.S. National Institutes of Health*, Clinical Study No. NCT01398969, pp. 1-4, last updated Feb. 27, 2014, Web, May 20, 2014 <http://clinicaltrials.gov/ct2/show/NCT01398969>.
Lewis et al., "Stool form scale as a useful guide to intestinal transit time," *Scand. J. Gastroenterol.*, 32(9):920-924 (1997).
Ley et al., "Ecological and evolutionary forces shaping microbial diversity in the human intestine," *Cell*, 124:837-848 (2006).
Ley et al., "Evolution of mammals and their gut microbes," *Science*, 320(5883):1647-1651 (2008).
Ley et al., "Microbial ecology: human gut microbes associated with obesity," *Nature*, 444(7122):1022-3 (2006).
Ley et al., "Worlds within worlds: evolution of the vertebrate gut microbiota," *Nat. Rev. Microbiol.*, 6(10):776-788 (2008).
Longstreth, "Irritable bowel syndrome: A multibillion-dollar problem," *Gastroenterology*, 109(6):2029-2031 (1995).
Loo et al., "A predominantly clonal multiinstitutional outbreak of *Clostridium difficile*-associated diarrhea with high morbidity and mortality," *N Engl J Med*, 353(23):2442-9 (2005).
Loo et al., "Host and pathogen factors for *Clostridium difficile* infection and colonization," *N Engl J Med*, 365(18): 1693-703 (2011).
Louie et al., "Fidaxomicin versus vancomycin for *Clostridium difficile* infection," *N. Engl. J. Med.*, 364(5):422-431 (2011).
Louie et al., "Home-based fecal flora infusion to arrest multiply-recurrent C. difficile infection," *ICAAC/IDSA Conference*, Abstract #K-4201 (2008).
Lu, "Taboo transplant: How new poo defeats superbugs," *Science News*, 1:90-91 (2011).
Lund-Tonnesen et al., "*Clostridium difficile*-associated diarrhea treated with homologous feces," *Tidsskr nor Lageforen*, 118:1027-1030 (1998).
MacConnachie et al., "Faecal transplant for recurrent *Clostridium difficile*-associated diarrhoea: a UK case series," *QJM*, 102(11):781-784 (2009).
MacDonald et al., "Formation of Ursodeoxycholic Acid from Chenodeoxycholic Acid by a 7β-Hydroxysteriod Dehydrogenase-Elaborating *Eubacterium aerofaciens* Strain Cocultured with 7α-Hydroxysteriod Dehydrogenase-Elaborating Organisms," *Applied and Environmental Microbiology*, 44(5): 1187-1195 (1982).
Macpherson et al., "Induction of protective IgA by intestinal dendritic cells carrying commensal bacteria," *Science*, 303:1662-1665 (2004).
Madsen, "The use of probiotics in gastrointestinal disease," *Can J Gastroenterol*, 15(12):817-22 (2001).

(56) References Cited

OTHER PUBLICATIONS

Marchesi et al., "The normal intestinal microbiota," *Curr. Opin. Infect. Dis.*, 20(5):508-513 (2007).
Martin, "Development and Delivery of a Treatment for *Clostridium difficile,*" *Bacteriotherapy*, pp. 1-2, n.d., Web, Feb. 10, 2012 <www.bacteriotherapy.org>.
Maslowski et al., "Diet, gut microbiota and immune responses," *Nat Immunol.*, 12(1):5-9 (2011).
McDonald et al., "An epidemic, toxin gene-variant strain of *Clostridium difficile,*" *N Engl J Med.*, 353(23):2433-41 (2005).
McDonald et al., "*Clostridium difficile* infection in patients discharged from US short-stay hospitals, 1996-2003[1]," *Emerg. Infect. Dis*, 12(3):409-415 (2006).
McFarland et al., "Breaking the cycle: treatment strategies for 163 cases of recurrent *Clostridium difficile* disease," *Am. J. Gastroenterol.*, 97(7):1769-1775 (2002).
McFarland et al., "Implications of the changing face of *Clostridium difficile* disease for health care practitioners," *Am J Infect Control.*, 35(4):237-253 (2007).
McFarland et al., "Meta-analysis of probiotics for the prevention of antibiotic associated diarrhea and the treatment of *Clostridium difficile* disease," *Am J Gastroenterol.*, 101(4):812-22 (2006).
McFarland et al., "Nosocomial acquisition of *Clostridium difficile* infection," *N Engl J Med.*, 320(4):204-210 (1989).
McFarland et al., "Recurrent *Clostridium difficile* disease: epidemiology and clinical characteristics," *Infect Control Hosp Epidemiol.*, 20(1):43-50 (1999).
McFarland et al., "Renewed interest in a difficult disease: *Clostridium difficile* infections—epidemiology and current treatment strategies," *Curr Opin Gastroenterol.*, 25(1):24-35 (2008).
Miller et al., "Health care-associated *Clostridium difficile* infection in Canada: patient age and infecting strain type are highly predictive of severe outcome and mortality," *Clin Infect Dis.*, 50(2):194-201 (2010).
Miller et al., "Long-term follow-up of patients with fulminant *Clostridium difficile* colitis," *J. Gastrointest. Surg.*, 13(5):956-959 (2009).
Miller et al., "Morbidity, mortality, and healthcare burden of nosocomial *Clostridium difficile*-associated diarrhea in Canadian hospitals," *Infect Control Hosp Epidemiol.*, 23(3):137-40 (2002).
Miller, "The fascination with probiotics for *Clostridium difficile* infection: lack of evidence for prophylactic or therapeutic efficacy," *Anaerobe*, 15(6):281-284 (2009).
Molecular Studies in Autism, 2004 Funding Cycle, Cure Autism Now, Cure Autism Now Foundation, pp. 1-7 (2005) <www.cureautismnow.org>.
Morris et al., "*Clostridium difficile* colitis: an increasingly aggressive iatrogenic disease?" *Arch Surg.*, 137(10):1096-1100 (2002).
Mullard, "Microbiology: the inside story," *Nature*, 453:578-580 (2008).
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activation of the Body's In-Built Defences," Ardeypharam GmbH 0796, D-58313 Herdecke Germany, 8 pgs (2006).
Mutaflor, "Safety of Therapy," Ardeypharm GmbH 0796, D-5 8313 Herdecke Germany, 4 pgs (1988).
Muto et al., "A large outbreak of *Clostridium difficile*-associated disease with an unexpected proportion of deaths and colectomies at a teaching hospital following increased fluoroquinolone use," *Infect Control Hosp Epidemiol.*, 26(3):273-80 (2005).
Nieuwdorp et al., ["Treatment of recurrent *Clostridium difficile*-associated diarrhoea with a suspension of donor faeces"], *Ned Tijdschr Geneeskd*, 152(35):1927-32 (2008).
O'Hara et al., "The gut flora as a forgotten organ," *EMBO Rep.*, 7(7):688-693 (2006).
O'Brien et al., "The emerging infectious challenge of *Clostridium difficile*-associated disease in Massachusetts hospitals: clinical and economic consequences," *Infect Control Hosp Epidemiol.*, 28(11):1219-27 (2007).
O'Connor et al., "*Clostridium difficile* infection caused by the epidemic BI/NAP1/027 strain," *Gastroenterology*, 136(6):1913-1924 (2009).
Patterson et al., "Special organism isolation: attempting to bridge the gap," *Infect Control Hosp Epidemiol.*, 15(5):335-338 (1994).
Pépin et al. "Emergence of fluoroquinolones as the predominant risk factor for *Clostridium difficile*-associated diarrhea: a cohort study during an epidemic in Quebec," *Clin Infect Dis.*, 41(9):1254-1260 (2005).
Pépin et al., "*Clostridium difficile* associated diarrhea in a region of Quebec from 1991 to 2003: a changing pattern of disease severity," *CMAJ*, 171(5):466-472 (2004).
Pépin et al., "Management and Outcomes of a First Recurrence of *Clostridium difficile*—Associated Disease in Quebec, Canada," *Clin. Infect. Dis.*, 42:758-764 (2006).
Persky et al., "Treatment of recurrent *Clostridium difficile*-associated diarrhea by administration of donated stool directly through a colonoscope," *Am J Gastroenterol.*, 95(11):3283-3285 (2000).
Petrof et al., "Stool substitute transplant therapy for the eradication of *Clostridium difficile* infection: 'RePOOPulating' the gut," *Microbiome*, 1:3 (2013).
Petrof, "Harnessing the healthy gut microbiota to cure patients with recurrent C. difficile infection," U.S. National Institutes of Health, Clinical Study No. NCT01372943, pp. 1-2, last updated Nov. 6, 2013, Web, May 22, 2014 <http://clinicaltrials.gov/ct2/show/NCT01372943>.
Pillai et al., "Probiotics for treatment of *Clostridium difficile*-associated colitis in adults (Review)," *Cochrane Database Syst Rev.*, (1):CD004611 (2008).
Porter, "Coating of pharmaceutical dosage forms," In D. B. Troy (Ed.), Remington: The Science and Practice of Pharmacy, Chapter 46, pp. 929-938 (2005).
Prakash et al., "Colon-targeted delivery of live bacterial cell biotherapeutics including microencapsulated live bacterial cells," *Biologics: Targets & Therapy*, 2(3):355-378 (2008).
Prevention of Sudden Infant Death Syndrome, Healthtouch.com, Thomson MICROMEDEX, pp. 1-4, n.d., Web, Nov. 23, 2005.
Rabeneck et al., "Bleeding and perforation after outpatient colonoscopy and their risk factors in usual clinical practice," *Gastroenterology*, 135(6):1899-1906 (2008).
Rager et al., "Evaluation of rumen transfaunation after surgical correction of left-sided displacement of the abomasum in cows," *J. Am. Vet. Med. Assoc.*, 225(6):915-920 (2004).
Rao et al., "Evaluation of gastrointestinal transit in clinical practice: position paper of the American and European Neurogastroenterology and Motility Societies," *Neurogastroenterol. Motil.*, 23(1):8-23 (2011).
Rea et al., "Gut solutions to a gut problem: bacteriocins, probiotics and bacteriophage for control of *Clostridium difficile* infection," *Journal of Medical Microbiology*, 62:1369-1378 (2013).
Redelings et al., "Increase in *Clostridium difficile*-related mortality rates, United States, 1999-2004," *Emerg Infect Dis.*, 13(9):1417-1419 (2007).
Rex et al., "American College of Gastroenterology guidelines for colorectal cancer screening 2008," *Am. J. Gastroenterol.*, 104(3):739-750 (2009).
Ricciardi et al., "Increasing prevalence and severity of *Clostridium difficile* colitis in hospitalized patients in the United States," *Arch Surg.*, 142(7):624-631 (2007).
Rodemann et al., "Incidence of *Clostridium difficile* infection in inflammatory bowel disease," *Clin Gastroenterol Hepatol.*, 5(3):339-344 (2007).
Rohlke et al., "Fecal flora reconstitution for recurrent *Clostridium difficile* infection: results and methodology," *J Clin Gastroenterol.*, 44(8):567-570 (2010).
Rolfe et al., "Bacterial interference between *Clostridium difficile* and normal fecal flora," *J Infect Dis.*, 143(3):470-475 (1981).

(56) References Cited

OTHER PUBLICATIONS

Round et al., "The gut microbiota shapes intestinal immune responses during health and disease," *Nat. Rev. Immunol.*, 9(5):313-323 (2009).
Rupnik et al., "*Clostridium difficile* infection: new developments in epidemiology and pathogenesis," *Nat. Rev. Microbiol.*, 7(7):526-536 (2009).
Russell et al., "Fecal bacteriotherapy for relapsing *Clostridium difficile* infection in a child: a proposed treatment protocol," *Pediatrics*, 126(1):e239-42 (2010).
Sambol et al., "Colonization for the prevention of *Clostridium difficile* disease in hamsters," *J. Infect. Dis.*, 186(12):1781-1789 (2002).
Sandler et al., "Possible Gut-Brain Interaction Contributing to Delayed Onset Autism Symptomatology," Fourth Int. Symp. Brain-Gut Interactions, Blackwell Science Ltd., 10(4):33 (1998).
Sandler et al., "Short-Term Benefit From Oral Vancomycin Treatment of Regressive-Onset Autism," *Journal of Child Neurology*, 15(7):429-435 (2000).
Schiller, "Review article, the therapy of constipation," *Ailment Pharmacol. Ther.*, 15:749-763 (2001).
Scholss, "Introducing mothur: Open-Source, Platform-Independent, Community-Supported Software for Describing and Comparing Microbial Communities," *Appl. Environ. Microbiol.*, 75(23):7537-7541 (2009).
Schwan et al., "Relapsing *Clostridium difficile* Enterocolitis Cured by Rectal Infusion of Homologous Faeces," *The Lancet*, 322(8354): 845 (1983).
Schwan et al., "Relapsing *Clostridium difficile* Enterocolitis Cured by Rectal Infusion of Normal Faeces," *Scand. J. Infect. Dis.*, 16(2):211-215 (1984).
Seeff et al., "How many endoscopies are performed for colorectal cancer? Results from CDC's survey of endoscopic capacity," *Gastroenterology*, 127:1670-1677 (2004).
Sekirov et al., "Gut microbiota in health and disease," *Physiol. Rev.*, 90(3):859-904 (2010).
Setlow, "I Will Survive: Protecting and Repairing Spore DNA," *Journal of Bacteriology*, 174(9):2737-2741 (1992).
Setlow, "The bacterial spore: nature's survival package," *Culture*, 26(2):1-4 (2005).
Shim et al., "Primary symptomless colonisation by *Clostridium difficile* and decreased risk of subsequent diarrhoea," *The Lancet*, 351(9103):633-666 (1998).
Silverman et al., "Success of self-administered home fecal transplantation for chronic *Clostridium difficile* infection," *Clin. Gastroenterol. Hepatol.*, 8(5):471-473 (2010).
Simor et al., "*Clostridium difficile* in long-term-care facilities for the elderly," *Infect Control Hosp Epidemiol.*, 23(11):696-703 (2002).
Singh et al., "Do NSAIDs, antibiotics, infections, or stress trigger flares in IBD?" *Am J Gastroenterol.*, 104(5):1298-1313 (2009).
Sleator, "The human superorganism—of microbes and men," *Med. Hypotheses*, 74(2):214-215 (2010).
Smits et al., "Therapeutic potential of fecal microbiota transplantation," *Gastroenterology*, 145:946-953 (2013).
Surawicz et al., "Treatment of refractory and recurrent *Clostridium difficile* infection," *Nat. Rev. Gastroenterol. Hepatol.*, 8(6):330-339 (2011).
Surawicz, "Reining in Recurrent *Clostridium difficile* Infection—Who's at Risk?," *Gastroenterology*, 136:1152-1154 (2009).
Sutherland et al., "Lyophilized Clostridium perfringens 3 alpha- and Clostridium bifermentans 7 alpha-hydroxysteroid dehydrogenases: two new stable enzyme preparations for routine bile acid analysis," *Biochim Biophys Acta*, 962(1):116-121 (1988).
Takeda et al., "Serum Haloperidol Levels of Schizophrenics Receiving Treatment for Tuberculosis," *Clinical Neuropharmacology*, 9(4):386-397 (1986).
Tannock et al., "A new macrocyclic antibiotic, fidaxomicin (OPT-80), causes less alteration to the bowel microbiota of *Clostridium difficile*-infected patients than does vancomycin," *Microbiology*, 156(11):3354-3359 (2010).
Teasley et al., "Prospective randomised trial of metronidazole versus vancomycin for Clostridium-difficile-associated diarrhoea and colitis," *The Lancet*, 2(8358):1043-1046 (1983).
Tilg et al., "Gut microbiome, obesity, and metabolic dysfunction," *J. Clin. Invest.*, 121(6):2126-2132 (2011).
Tvede et al., "Bacteriotherapy for chronic relapsing *Clostridium difficile* diarrhea in six patients," *The Lancet*, 1:1156-1160 (1989).
Van der Waaij et al., "Direct Flow Cytometry of Anaerobic Bacteria in Human Feces," *Cytometry*, 16:270-279 (1994).
Van Nood et al., "Struggling with Recurrent *Clostridium difficile* Infections: Is Donor Faeces the Solution?," *Euro Surveill.*, 14(34):1-6 (2009).
Van Nood, "Duodenal infusion of donor feces for recurrent *Clostridium difficile*," *New England Journal of Medicine*, 368(5):407-415 (2013).
Veldhuyzen van Zanten et al., "Drug treatment of functional dyspepsia: a systematic analysis of trial methodology with recommendations for design of future trials," *Am. J. Gastroenterol.*, 91(4):660-673 (1996).
Veldhuyzen van Zanten et al., "Validation of a 7-point Global Overall Symptom scale to measure the severity of dyspepsia symptoms in clinical trials," *Ailment Pharmacol. Ther.*, 23(4):521-529 (2006).
Venugopal et al., "Fidaxomicin: a novel macrocyclic antibiotic approved for treatment of *Clostridium difficile* infection," *Clin Infect Dis*, 54(4):568-74 (2012).
Vrieze et al., "The environment within: how gut microbiota may influence metabolism and body composition," *Diabetologia*, 53(4):606-613 (2010).
Walter et al., "Host-microbial symbiosis in the vertebrate gastrointestinal tract and the Lactobacillus reuteri paradigm;" *PNAS USA*, 108(Suppl 1):4645-4652 (2011).
Warny et al., "Toxin production by an emerging strain of *Clostridium difficile* associated with outbreaks of severe disease in North America and Europe," *Lancet*, 366(9491):1079-84 (2005).
Wasfy et al., "Comparison of Preservation Media for Storage of Stool Samples," *Journal of Clinical Microbiology*, 33(8):2176-2178 (1995).
Weissman et al., "Stool Transplants: Ready for Prime Time?," *Current Gastroenterology Reports*, 14:313-316 (2012).
Wenisch et al., "Comparison of vancomycin, teicoplanin, metronidazole, and fusidic acid for the treatment of *Clostridium difficile*-associated diarrhea," *Clin Infect Dis.*, 22(5): 813-818 (1996).
Wettstein et al., "Fecal bacteriotherapy—an effective treatment for relapsing symptomatic *Clostridium difficile* infection," Abstract, 15th United European Gastroenterology Week (UEGW) Poster presentations, United European Gastroenterology Federation, France, A303 (2007).
Wikoff et al., "Metabolomics analysis reveals large effects of gut microflora on mammalian blood metabolites," *PNAS*, 106(10):3698-3703 (2009).
Wilson et al., "Human colonic biota studied by ribosomal DNA sequence analysis," *Appl. Environ. Microbiol.*, 62(7):2273-2278 (1996).
Yoon et al., "Treatment of refractory/recurrent C. difficile-associated disease by donated stool transplanted via colonoscopy: a case series of 12 patients," *J Clin Gastroenterol.*, 44(8):562-566 (2010).
You et al., "Successful treatment of fulminant *Clostridium difficile* infection with fecal bacteriotherapy," *Ann. Intern. Med.*, 148(8):632-633 (2008).
Yue et al., "Similarity Measure Based on Species Proportions," *Commun. Stat. Theor. Methods*, 34(11):2123-2131 (2005).
Zar et al., "A comparison of vancomycin and metronidazole for the treatment of *Clostridium difficile*-associated diarrhea, stratified by disease severity," *Clin Infect Dis.*, 45(3):302-307 (2007).
Zilberberg et al., "*Clostridium difficile*-related hospitalizations among US adults, 2006," *Emerg. Infect. Dis*, 15(1):122-124 (2009).
Zilberberg et al., "Increase in adult *Clostridium difficile*-related hospitalizations and case-fatality rate, United States, 2000-2005.," *Emerg. Infect. Dis*, 14(6):929-931 (2008).

(56) References Cited

OTHER PUBLICATIONS

Zilberberg et al., "Increase in *Clostridium difficile*-related hospitalizations among infants in the United States, 2000-2005," *Pediatr Infect Dis J.*, 27(12):1111-1113 (2008).
Zilberberg et al., "*Clostridium difficile* Infections among Hospitalized Children, United States, 1997-2006" *Emerg. Infect. Dis*, 16:604-610 (2010).
Zoppi et al., "Oral Bacteriotherapy in Clinical Practice," *Eur J. Pediatr*, 139(1):18-21 (1982).
Zoppi et al., "Oral Bacteriotherapy in Clinical Practice," *Eur J. Pediatr*, 139(1):22-24 (1982).
Zoppi et al., "The Intestinal Ecosystem in Chronic Functional Constipation," *ACTA Paediatr*, Scandinavian University Press, p. 836-841 (1998).

\* cited by examiner

PROBIOTIC RECOLONISATION THERAPY

CROSS-REFERENCE TO RELATED APPLICATIONS

This United States utility patent application is a continuation of U.S. patent application Ser. No. 14/793,630, filed Jul. 7, 2015, and is a continuation of U.S. Ser. No. 14/793,642, filed Jul. 7, 2015, and is a continuation of Ser. No. 14/793,623, filed Jul. 7, 2015, and is a continuation of U.S. Ser. No. 14/710,481, filed May 12, 2015, and is a continuation of U.S. Ser. No. 14/710,487, filed May 12, 2015. U.S. Ser. Nos. 14/793,630, 14/793,642, and 14/793,623 are each continuations of U.S. Ser. No. 14/710,481 and U.S. Ser. No. 14/710,487. U.S. Ser. Nos. 14/710,481 and 14/710,487 are each continuations of U.S. Ser. No. 14/270,034, filed May 5, 2014, now U.S. Pat. No. 9,050,358, issued Jun. 9, 2015 (which is a Continuation of U.S. Ser. No. 13/910,579, filed Jun. 5, 2013, now U.S. Pat. No. 9,040,036, issued May 26, 2015); and U.S. Ser. No. 13/910,579, filed Jun. 5, 2013, now U.S. Pat. No. 9,040,036, issued May 26, 2015; which is a divisional of U.S. Ser. No. 10/332,986, filed Aug. 4, 2003, now U.S. Pat. No. 8,460,648, issued Jun. 11, 2013; which is a § 371 national phase of PCT international patent application no. PCT/AU01/00907, having an international filing date of Jul. 25, 2001, which claims benefit of priority to Australian Patent Application Serial No. PQ 8997, filed Jul. 25, 2000. The aforementioned applications are expressly incorporated herein by reference in their entirety and for all purposes.

TECHNICAL FIELD

The present invention relates to pharmaceutical compositions suitable for the treatment of diseases in mammals, in particular to the treatment of chronic disorders associated with the presence of abnormal or an abnormal distribution of microflora in the gastrointestinal tract. The invention also relates to methods of treating such diseases.

BACKGROUND ART

There are large numbers of patients suffering from gastrointestinal symptoms referable to the lower small bowel and large bowel which to date have eluded explanation. These disorders include irritable bowel syndrome (IBS) or spastic colon, idiopathic ulcerative colitis, mucous colitis, collagenous colitis, Crohn's disease, inflammatory bowel disease in general, microscopic colitis, antibiotic-associated colitis, idiopathic or simple constipation, diverticular disease, and AIDS enteropathy. Pathophysiology of these disorders eludes logical explanation in spite of decades of research and millions of dollars of research funds. A common underlying factor shared by all these disorders observed by the present inventor is their onset or aggravation following some extraneous invading infection eg travelers diarrhoea. In all the disorders, a specific causal infection generally cannot be demonstrated due to our inability to detect infecting agents whose cultural characteristics are unknown to medical science.

Circumstantial evidence which suggests that these disorders are "infection-related" includes:

(a) onset following a gastro-intestinal infection which failed to completely resolve;

(b) transient improvement with use of certain antibiotics, but recurrence upon cessation of antibiotics;

(c) transient improvement following orthostatic lavage prior to colonoscopy and;

(d) transient symptom improvement with use of "colonic" irrigation.

It is impractical to use long-term antibiotic therapy (with its associated complications) in such patients since cure is not obtained with its use. Furthermore, chronic gut infections with recognised, specific pathogens such as *Clostridium difficile, Yersinia enterocolitica* or *Campylobacter jejuni/coli* are generally not eradicated with antibiotics. Some previous attempts have been made to alter the enteric microflora in order to eradicate such chronic infections. These measures nevertheless indicate that alteration of bacterial flora may effect dramatic clinical improvement in conditions characterised by chronic, resistant enterocolitic infection. However there remain many chronic disorders of uncertain aetiology or causation, which are resistant to cure by current therapeutic techniques.

The use of probiotics in the human population has been largely confined to the inclusion in various foods of live organism of Lactobacilli and Bifidobacteria and less frequently *Streptococcus faecalis* or several strains of *Escherichia coli*. These organisms are thought to promote health via immune stimulation and reconstitution of what is presumed to be normal flora. Such usage stems back to the beliefs generated by Mechnikov in the early 1900s. The use of probiotics to treat established infections in the gastrointestinal tract has been lesser but a growing part of the use of probiotics. Fungal agents such as *Saccharomyces boulardii* have been used to treat, albeit inefficiently, *Clostridium difficile* infection and *Lactobacillus* GG has also been used for this purpose (Floch M. Probiotics and Dietary Fibre. *J Clin Gastroenterol* 1998; 27(2):99-100). Various patents have claimed the use of probiotics for narrow disease conditions including treatment of *Clostridium difficile* with a combination of Vancomycin and butyric acid bacteria (U.S. Pat. No. 5,266,315), diarrhoea prevention using *Lactobacillus* (U.S. Pat. No. 5,837,238) or *Bifidobacterium* (U.S. Pat. No. 5,902,743), *Lactobacillus acidophilus* to inhibit *cryptosporidium* (U.S. Pat. No. 5,858,356) and mixtures of Lactobacilli and Bifidobacteria in infants to prevent diarrhoea. *Enterococcus faecium* has been claimed to be useful in alleviating symptoms of Irritable Bowel Syndrome in humans (U.S. Pat. No. 5,902,578) (U.S. Pat. No. 5,728,380) but this has not recognised *Clostridium* as the underlying agent in this condition. *Clostridium butyricum* as a single agent has been claimed to be a biological intestinal antiseptic for treatment of bacterial food poisonings (U.S. Pat. No. 4,892,731), but its use in chronic disease treatment was not contemplated.

Previous attempts to alter the enteric microflora of a patient have prescribed the removal of at least a part of the host's existing enteric microflora, for instance by lavage, prior to substitution with predetermined desired microflora. This procedure, which was the preferred embodiment of WO90/01335 has the distinct disadvantages of complicating the treatment and of causing further discomfort to the patient. This patent also advocated the use of dried, reconstituted faeces or a synthetic mixture comprising *Bacteroides* sp. and *Escherichia coli*. It has now been surprisingly found that lavage or other methods of removal of at least a part of the host's existing enteric microflora can be omitted provided a non-pathogenic *Clostridium* sp. is included within the probiotic replacement mixture. Such a replacement mixture has the dual ability of displacing pathogenic bacteria, frequently Clostridial in nature and also establishing a normal environment in which commensal bacteria can establish. Such a treatment permits long-term recovery both from gastrointestinal disorders and from systemic afflictions not hitherto considered to be caused by harmful enteric flora. These are also called 'para-infective' phenomena and can include rheumatological, neurological, regressive, hepatic, and dermatological conditions among others.

Autism is a regressive disorder of childhood, affecting boys four times more often than girls. It has been observed that the onset of autism is often preceded by broad spectrum antibiotic use eg for recurrent ear infections. Antibiotic therapy is non-discriminatory in its action and apart from treating the ear infection the microflora of the healthy gastrointestinal tract can be severely disrupted by such treatment. This creates an environment where vulnerability to opportunistic microorganism colonisation is heightened.

*Clostridium tetani* is a widely distributed, spore forming anaerobe. Toxigenic strains of *Clostridium tetani* produce the extremely potent tetanus neurotoxin which is known to enter the central nervous system from the intestinal tract via the vagus nerve (Hensel B et al. Naunyn Schmeidebergs Arch Pharmocol 1973; 276:395). Bolte (Med Hypotheses 1998; 51:133) has hypothesised that opportunistic infection by *Clostridium tetani* may be responsible for the behavioural and medical symptoms present in a sub-group of individuals diagnosed with autism. Others have also raised the possibility of clostridia in general as a cause of disease (Borriello SP. Clin Infect Dis 1995; Suppl 2:5242).

Sandler et al. (Fourth Int. Symp. Brain-Gut Interactions. 1998; 10: 363) report a trial in which children with delayed onset autism were treated with vancomycin over an 8 week period. All children in the trial had had antecedent broad-spectrum antibiotic exposure, followed by chronic persistent diarrhoea and then onset of autistic features. Although significant post-treatment improvement was noted, all children eventually regressed towards baseline.

It is on the background of these known facts and later the results of trials of treatment, that the present invention was formulated. In brief, it was noted that autistic children (as well as related syndromes) who were referred for treatment of refractory 'irritable bowel syndrome' (IBS) viz diarrhoea, flatulence, constipation, distension, abdominal pains etc—responded to treatment of their IBS when treated with a novel mix of probiotics. However, not only did their IBS improve dramatically but also their autistic features progressively regressed. Even after the initial 2-6 weeks of treatment eye contact was re-established, repetitive movements were much reduced, and word power (observed vocabulary) expanded—initially 20 words and ultimately >600 words at 12 months (estimated), creating ability of the autistic children to form long sentences. Continuing improvement was observed to occur over 12 months of treatment. These observations (to a lesser but definite degree at this stage of observations) also applied to those with Rett syndrome and children with Attention Deficit/Hyperactivity Disorder (ADHD), Attention Deficit Disorder (ADD), and autism variant Asbergers syndrome. The observations strongly suggest that the treatment of presumed enteric infection/s (eg Clostridial) in these conditions not only improves the IBS present but also the attendant neurological 'para-infective' phenomena called collectively autism, Asbergers, Rett syndrome, ADD or ADHD.

The inclusion within this specification of reference to published documents is not to be taken to be an admission that any one or more of those documents, nor the disclosure of any one or more of those documents, is part of the common general knowledge.

OBJECTS OF THE INVENTION

It is thus an object of the present invention to provide novel pharmaceutical compositions suitable for the treatment of various disease states related to the presence of 'abnormal' microflora in the gastrointestinal tract. It is a further object of the invention to propose the use of these pharmaceutical compositions in various disease states which have not previously been considered to owe their causation to the presence of abnormal flora in the gastrointestinal tract.

DISCLOSURE OF THE INVENTION

The present invention recognises chronic infection/infestation as the underlying pathological process in a wide range of chronic disorders such as irritable bowel syndrome, particularly when characterised by chronic abdominal pain, bloating, or excessive flatulence, together with chronic diarrhoea or alternating constipation/diarrhoea, and also in spastic colon, mucous colitis, collagenous colitis, ulcerative colitis, Crohn's colitis, microscopic colitis, idiopathic inflammatory bowel disease, antibiotic-associated colitis, idiopathic or simple constipation, diverticular disease and AIDS enteropathy.

The invention has also been found to relate to other gastrointestinal disorders of unexplained aetiology such as polyposis coli and colonic polyps, which may well be influenced by the local bowel microflora.

In addition the present invention also provides a method of treatment of chronic gastrointestinal infections with specific microorganisms such as *Clostridium difficile, Yersinia* spp, *Campylobacter* spp, *Aeromonas* spp, *Escherichia coli, Cryptosporidium* spp, Amoebae, *Blastocystitis homini's, Giardia* and even chronic viral infections, and of small bowel bacterial overgrowth.

The present invention furthermore, recognises the close association between the intestine and liver disease, and the intestine and migraines and chronic fatigue syndrome, and possibly other neurological syndromes such as, multiple sclerosis, amyotrophic lateral sclerosis, myasthenia gravis, Parkinson's disease, Alzheimer's disease, Chronic Inflammatory Demyelinating Polyneuropathy (CIDP), Guillain Barre Syndrome, and other degenerative disorders. Hence, it is proposed that a considerable proportion of currently unexplained diseases of the liver and nervous system of unknown aetiology may be explicable by the chronic growth of pathogens within the small/large intestine and the subsequent passage of antigenic material, pathogenic toxins or biological response modifiers (BRMs) into the portal system (liver damage) or systemic circulation with antibody formation (neurological conditions). Specifically, such hepato/biliary system disorders as primary biliary cirrhosis, primary sclerosing cholangitis, fatty liver of unknown aetiology, or cryptogenic cirrhosis, may be secondary to chronic pathogen carrier state in the intestine.

The links between the intestine and joint disease are also recognised. Joint diseases such as rheumatoid arthritis, the non-rheumatoid arthritidies including, ankylosing spondylitis, and Reiter's syndrome, may also be causally related to a chronic intestinal carrier state, as may other syndromes with an immune mediated component such as glomerulonephritis, haemolytic uraemic syndrome, juvenile diabetes mellitus, Behcet's syndrome, coeliac disease and dermatitis herpetiformis. Similarly, syndromes with an immune complex mediated component, such as scleroderma, systemic lupus erythematosus, mixed cryoglobulinaemia, polyarteritis, familial Mediterranean fever, amyloidosis, and the various presentations of such syndromes, together with such "idiopathic" states as chronic urticaria, may be manifestations of variations of immune regulated responses to related bowel-origin pathogens chronically shedding their antigen(s), toxins or biological response modifiers into the circulation. Other chronic conditions such as acne, and chronic idiopathic pseudo-obstructive syndrome, may well be influenced by similar mechanisms.

For many of these syndromes present therapy offers only palliation of symptoms and/or the induction of remission of the disease process but not cure. The present inventor therefore recognised the need to find a curative therapy for these wide ranging disease processes associated with considerable morbidity.

By judicious selection of the microorganisms of the invention it has been surprisingly found by the present inventor that lasting recolonisation of the gut microflora does not require pretreatment to remove a portion of the host's existing enteric microflora. Thus, by incorporation of Clostridia spp. in the therapy, it has been surprisingly found that the prior art requirement for removal of at least a portion of the existing enteric microflora before administration of the substitute microflora is rendered unnecessary. Without the addition specifically of Clostridia species, the use of probiotic mixtures, eg such as those of *bacteroides* and *Escherichia coli* failed to have the necessary impact on the above-mentioned clinical disorders for the treatment to be clinically useful. It required a prior purging of the gut of its presumably infected and abnormal bowel flora, re colonisation with *bacteroides* and *Escherichia coli*—the main components of lower intestinal tract, and ongoing feeding of patients with such bacteria until colonisation was established. The use of Clostridia appears to be the mainstay of this new therapy and the Clostridia appear to have power of themselves to remove offending bacterial species which may be responsible for the underlying condition (presumably pathogenic clostridia—yet to be identified scientifically). Hence, the combination of non-pathogenic clostridia together with the crucial major colonic bacterial components of *bacteroides* and *Escherichia coli* can now be used as oral therapy to crowd out/destroy/replace and recolonise the dysbiotic flora of patients with various gastrointestinal conditions which are caused by abnormal bowel flora. In fact, such a therapy becoming available has permitted or allowed greater understanding of the pathogenesis of many other conditions which hitherto were thought to be caused by degenerative, inflammatory, or auto immune mechanisms.

Thus according to a first embodiment of the invention there is provided a pharmaceutical composition useful for the treatment and/or prophylaxis of chronic disorders associated with the presence in the gastrointestinal tract of a mammalian host of abnormal or an abnormal distribution of microflora, which composition comprises viable non-pathogenic or attenuated pathogenic Clostridia.

Typically the composition includes Clostridia selected from the group consisting of *Clostridium absonum, Clostridium argentinense, Clostridium baratii, Clostridium bifermentans, Clostridium botulinum, Clostridium butyricum, Clostridium cadaveris, Clostridium camis, Clostridium celatum, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium ramosum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tedium, Clostridium tetani, Clostridium welchii, Clostridium villosum.*

In a preferred form the composition further comprises one or more additional viable non-pathogenic or attenuated pathogenic microorganisms selected from the group consisting of *Bacteroides*, Eubacteria, Fusobacteria, Propionibacteria, Lactobacilli, anaerobic cocci, *Ruminococcus, Escherichia coli, Gemmiger, Desulfomonas, Peptostreptococcus,* species and, more specifically, bacteria selected from Table 1. Preferably fungi are also present such as *Monilia*.

In a preferred form the composition comprises Clostridia, *Bacteroides, Peptostreptococcus, Escherichia coli, Bifidobacterium*, and *Lactobacillus*.

In a more preferred form the composition comprises *Clostridium innocuum, Clostridium bifermentans, Clostridium butyricum, Bacteroides fragilis, Bacteroides thetaiotaomicron, Bacteroides uniformis*, one or more strains of *Escherichia coli*, and one or more strains of *Lactobacillus*.

Alternatively, in a preferred form the composition comprises *Clostridium bifermentans, Clostridium innocuum*, and *Clostridium butyricum* in combination one or more strains of *Escherichia coli*, one or more strains of *bacteroides* and *Peptostreptococcus productus*.

According to a second embodiment of the invention there is provided a pharmaceutical composition useful for the treatment and/or prophylaxis of chronic disorders associated with the presence in the gastrointestinal tract of a mammalian host of abnormal or an abnormal distribution of microflora, which composition comprises viable non-pathogenic or attenuated pathogenic *Escherichia coli*, at least one strain of viable non-pathogenic or attenuated pathogenic *Bacteroides*, and at least one other viable non-pathogenic or attenuated pathogenic microorganism.

In a preferred form the other viable non-pathogenic or attenuated pathogenic microorganism is selected from the group consisting of Clostridia, *Peptostreptococcus, Bifidobacterium*, and *Lactobacillus*.

Typically the composition of the first or second embodiments of the invention is derived from disease screened fresh homologous faeces, equivalent freeze-dried and reconstituted faeces or a "synthetic" faecal composition. The fresh homologous faeces does not include an antibiotic resistant population.

Typically, the composition of the first or second embodiments of the invention is a synthetic faecal composition.

In a preferred form the synthetic faecal composition comprises a preparation of viable flora which preferably in proportional content, resembles normal healthy human faecal flora which does not include antibiotic resistant populations. Suitable microorganisms may be selected from the following: *Bacteroides*, Eubacteria, Fusobacteria, Propionibacteria, Lactobacilli, anaerobic cocci, *Ruminococcus, Escherichia coli, Gemmiger, Clostridium, Desulfomonas, Peptostreptococcus, Bifidobacterium*, species and, more specifically, bacteria selected from Table 1. Preferably fungi are also present such as *Monilia*.

In a preferred form the composition of the first or second embodiments of the invention comprises a liquid culture.

Preferably, the composition of the first or the second embodiments of the present invention is lyophilised, pulverised and powdered. It may then be infused, dissolved such as in saline, as an enema.

Alternatively the powder may be encapsulated as enteric-coated capsules for oral administration. These capsules may take the form of enteric-coated microcapsules. As a powder it can preferably be provided in a palatable form for reconstitution for drinking or for reconstitution as a food additive. The composition can be provided as a powder for sale in combination with a food or drink. Typically, the food or drink is a dairy-based product or a soy-based product. The invention therefore also includes a food or food supplement containing a composition according to the first or second embodiment. In a preferred form the food or food supplement contains enteric-coated microcapsules of the composition of the invention. In a preferred form the food is yogurt.

The powder may be reconstituted also to be infused via naso-duodenal infusion.

The composition can be combined with other adjuvants such as antacids to dampen bacterial inactivation in the stomach., eg Mylanta, Mucaine, Gastrogel. Acid secretion in the stomach could also be pharmacologically suppressed using H2-antagonists or proton pump inhibitors. Typically, the H2-antagonist is ranitidine. Typically the proton pump inhibitor is omeprazole.

The composition of the first or second embodiments of the invention is therefore preferably in the form of:
  an enema composition which can be reconstituted with an appropriate diluent, or
  enteric-coated capsules, or
  enteric-coated microcapsules, or
  powder for reconstitution with an appropriate diluent for naso-enteric infusion or colonoscopic infusion, or
  powder for reconstitution with appropriate diluent, flavouring and gastric acid suppression agent for oral ingestion, or
  powder for reconstitution with food or drink, or
  food or food supplement comprising enteric-coated microcapsules of the composition, powder, jelly, or liquid.

According to a third embodiment of the invention there is provided a method for the treatment and/or prophylaxis of a chronic disorder associated with the presence in the gastro-intestinal tract of a mammalian host of abnormal or an abnormal distribution of microflora, which method comprises administering an effective amount of a composition according to the first or second embodiment of the invention.

In its preferred form the treatment should effect a cure of the symptoms of such disorders. The change of flora is preferably as "near-complete" as possible and the flora is replaced by viable organisms which will crowd out any remaining, original flora.

The method of the present invention is applicable to animals in general, in particular humans and economically significant domestic animals.

In the case of humans, the present invention encompasses methods of treatment of chronic disorders associated with the presence of abnormal enteric microflora. Such disorders include but are not limited to those conditions in the following categories:
  gastro-intestinal disorders including irritable bowel syndrome or spastic colon, functional bowel disease (FBD), including constipation predominant FBD, pain predominant FBD, upper abdominal FBD, non-ulcer dyspepsia (NUD), gastro-oesophageal reflux, inflammatory bowel disease including Crohn's disease, ulcerative colitis, indeterminate colitis, collagenous colitis, microscopic colitis, chronic *Clostridium difficile* infection, pseudomembranous colitis, mucous colitis, antibiotic associated colitis, idiopathic or simple constipation, diverticular disease, AIDS enteropathy, small bowel bacterial overgrowth, coeliac disease, polyposis coli, colonic polyps, chronic idiopathic pseudo obstructive syndrome;
  chronic gut infections with specific pathogens including bacteria, viruses, fungi and protozoa;
  viral gastrointestinal disorders, including viral gastroenteritis, Norwalk viral gastroenteritis, rotavirus gastroenteritis, AIDS related gastroenteritis;
  liver disorders such as primary biliary cirrhosis, primary sclerosing cholangitis, fatty liver or cryptogenic cirrhosis;
  rheumatic disorders such as rheumatoid arthritis, non-rheumatoid arthritidies, non rheumatoid factor positive arthritis, ankylosing spondylitis, Lyme disease, and Reiter's syndrome;
  immune mediated disorders such as glomerulonephritis, haemolytic uraemic syndrome, juvenile diabetes mellitus, mixed cryoglobulinaemia, polyarteritis, familial Mediterranean fever, amyloidosis, scleroderma, systemic lupus erythematosus, and Behcets syndrome;
  autoimmune disorders including systemic lupus, idiopathic thrombocytopenic purpura, Sjogren's syndrome, haemolytic uremic syndrome or scleroderma;
  neurological syndromes such as chronic fatigue syndrome, migraine, multiple sclerosis, amyotrophic lateral sclerosis, myasthenia gravis, Gillain-Barre syndrome, Parkinson's disease, Alzheimer's disease, Chronic Inflammatory Demyelinating Polyneuropathy, and other degenerative disorders;
  psychiatric disorders including chronic depression, schizophrenia, psychotic disorders, manic depressive illness;
  regressive disorders including Asbergers syndrome, Rett syndrome, attention deficit hyperactivity disorder (ADHD), and attention deficit disorder (ADD);
  the regressive disorder, autism;
  sudden infant death syndrome (SIDS), anorexia nervosa;
  dermatological conditions such as, chronic urticaria, acne, dermatitis herpetiformis and vasculitic disorders.

The above disorders are all characterised by their response to treatment with the method of the present invention.

Typically the change in enteric flora comprises introduction of an array of predetermined flora into the gastro-intestinal system, and thus in a preferred form the method of treatment comprises substantially completely displacing pathogenic enteric flora in patients requiring such treatment.

Furthermore, in some of these disorders a short course of antibiotics prior to probiotic treatment may be preferred to rid tissue-invasive pathogens originating in the bowel lumen. For example, in Crohn's disease, anti-tuberculosis therapy may be required for six to twelve weeks before the bowel is cleared out and the flora content exchanged for a predetermined flora.

Typically the antibiotic is an anti-Clostridial antibiotic such as vancomycin, rifampicin, and nitroimidazole or chloramphenicol. Typically the nitroimidazole is metronidazole.

In a preferred form of the invention, the method of treatment or prophylaxis further includes administration of at least one acid suppressant prior to administering, or in co-administration with, the composition of the invention.

In a preferred form of the invention the method of treatment or prophylaxis further includes nasogastric and/or nasoduodenal washout prior to administering said composition.

The introduction of the composition into the gastrointestinal system can be effected by enema or per-colonoscope, via intubation of the small bowel using for example a large bore catheter equipped with distal balloon to effect rapid passage down the jejunum, or via the oral route with enteric-coated capsules, including enteric-coated microcapsules, or via the oral route with a supplemented food or drink.

In a preferred form the supplemented food or drink is a dairy-based or soy-based product. Typically the supplemented food product is yogurt.

According to the method of the invention each dose of the composition is in the range of about $10^3$ cells to about $10^{13}$ cells. Preferably each dose is in the range of about $10^5$ cells to about $10^{11}$ cells. More preferably each dose is in the range of about $10^9$ cells to about $10^{11}$ cells. In a preferred form of the invention an initial treatment regimen consisting of about $10^{10}$ cells per dose is administered about 3 to 6 times per day for a period sufficient to stabilise the gut flora. According to the method of the invention the treatment regimen may then comprise a maintenance dose of about $10^{10}$ cells per day.

Furthermore the present invention also relates to the treatment of animals, in particular to the treatment of gastrointestinal disorders in economically important domestic animals, such as cattle, sheep, horses, pigs, goats etc. The method of the present invention has been found to be especially useful in the treatment of the various forms of necrotising enterocolitis which can be a major problem in animal stocks.

Obviously in the treatment of animals the appropriate composition of microflora will vary according to the species being treated and the constituent normal flora known to inhabit the gut. Thus the composition according to the invention would comprise, a preparation of viable flora which preferably in proportional content, resembles the normal healthy faecal flora of the species involved. The compositions may be prepared in any of the forms already described and administered accordingly.

BEST METHOD OF PERFORMING THE INVENTION

In the practice of the invention a synthetic faecal composition of predetermined flora in the form of a liquid or dry powdered culture of Clostridia, *Bacteroides, Peptostreptococcus, Escherichia coli, Bifidobacterium*, and *Lactobacillus*, which composition does not include antibiotic resistant populations, is prepared as a liquid culture.

Typically the method of the invention is applicable to a patient suffering from a chronic disorder associated with the presence of abnormal microflora in the gastrointestinal tract such as irritable bowel syndrome.

In the practice of the invention a composition of predetermined flora in the form of a liquid culture of Clostridia, *Bacteroides, Peptostreptococcus, Escherichia coli, Bifidobacterium*, and *Lactobacillus* is ingested by the patient in an amount sufficient to replace and recolonise the dysbiotic flora of the gastrointestinal tract, and reverse the disease process. Alternatively fresh homologous faeces obtained from a disease screened donor are liquefied and mixed with unprocessed bran. The mixture is then homogenised anaerobically under $CO_2$ cover and infused into the patient per colonoscope.

Cure or remission of symptoms is then monitored subjectively and by assessment of stool frequency or other appropriate criteria.

Using liquid cultures of Clostridia, *Bacteroides, Peptostreptococcus, Escherichia coli, Bifidobacterium*, and *Lactobacillus* the inventor has achieved total reversal of colitis, irritable bowel syndrome and constipation.

As indicated in the method of treatment aspect of the invention, a preparatory course of appropriate antibiotics may be used. For example, Septrin for chronic yersiniasis, Metronidazole for ulcerative colitis, anti-TB therapy in Crohn's disease, or Vancomycin in chronic *Clostridium difficile* infestations.

TABLE 1

| % of flora [b] | Organism(s) |
|---|---|
| 11.8(0.90) | *Bacteroides fragilis* ss. *Vulgatus* |
| 9.9(0.83) | *Collinsella aerofaciens* |
| 8.9(0.78) | *Bacteroides fragilis* ss. *Thetaiotaomicron* |
| 6.6(0.68) | *Peptostreptococcus productus* II |
| 6.0(0.64) | *Parabacteroids distasonis* |
| 4.4(0.55) | *Faecalibacterium prausnitzii* |
| 3.5(0.49) | *Coprococcus eutactus* |
| 3.0(0.45) | *Collinsella aerofaciens* |
| 2.8(0.44) | *Peptostreptococcus productus* I |
| 2.7(0.43) | *Ruminococcus bromii* |
| 2.6(0.43) | *Bifidobacterium adolescentis* |
| 2.2(0.39) | *Gemmiger forrnicilis, Bifidobacterium longum* |
| 2.1(0.38) | *Eubacterium siraeum* |
| 1.8(0.35) | *Ruminococcus torques* |
| 1.7(0.34) | *Eubacterium rectale* |
| 1.6(0.33) | *Eubacterium rectale* IV, *Eubacterium eligens* |
| 1.5(0.32) | *Bacteroides eggerthii* |
| 1.4(0.31) | *Clostridium leptum* |
| 1.3(0.29) | *Bacteroides fragilis* ss. A |
| 1.2(0.29) | *Eubacterium biforme* |
| 0.91(0.25) | *Bifidobacterium infantis* |
| 0.84(0.24) | *Eubacterium rectale* |
| 0.57(0.20) | *Coprococcus comes, Pseudoflavonifractor capillosus* |
| 0.50(0.18) | *Ruminococcus albus, Dorea formicigenerans, Eubacterium hallii, Eubacterium ventriosum* I, *Fusobacterium russii* |

TABLE 1-continued

| % of flora [b] | Organism(s) |
|---|---|
| 0.43(0.17) | *Ruminococcus obeum, Eubacterium rectale* II,*Clostridium ramosum* I, *Lactobacillus leichmannii* |
| 0.36(0.16) | *Ruminococcus caillidus, Butyrivibrio crossotus* |
| 0.30(0.14) | *Acidaminococcus fermentans, Eubacterium ventriosum, Bacteroides fragilis* ss. *fragilis* |
| 0.23(0.12) | *Coprococcus catus, Aerostipes hadrus, Eubacterium cylindroides, Eubacterium ruminantium, Staphylococcus epidermidis* |
| 0.17(0.10) | *Peptostreptococcus* BL, *Eubacterium limosum, Tissirella praeacuta, Bacteroides* L, *Fusobacterium mortiferum* I, *Fusobacterium navifomie, Clostridium innocuum, Clostridium ramosum, Propionibacterium acnes, Ruminococcus flavefaciens* |
| 0.10(0.08) | *Ruminococcus* AT, *Peptococcus* AU-1, *Bacteroides fragilis* ss. *ovatus*, ss. d, *Bacteroides fragilis* ss. f; *Bacteroides* L-1, *Bacteroides* L-5; *Fusobacterium nucleatum, Fusobacterium mortiferum, Escherichia coli, Gemella morbillorum* |
| 0.05(0.05) | *Finegoldia magnus, Peptococcus* G, -AU-2; *Streptococcus intermedius, Ruminococcus lactaris, Gemmiger, Coprococcus* BH, -CC; *Eubacterium tenue, Eubacterium ramulus, Clostridium clostridiiforme, Bacteroides coagulans, Prevotella oralis, Prevotella brevis, Prevotella ruminicola, Odoribacter splanchnicus Desuifomonas pigra, Fusobacterium* H, *Lactobacillus* G, *Succinivibrio* A |

[b] The percentage of the faecal population (the standard deviation of the estimate is given in parentheses).

The invention will now be further described with reference to the following non-limiting examples.

EXAMPLES

Formulations

The probiotic therapeutic agents may be prepared in liquid culture anaerobically or aerobically (depending on bacterium cultured) in pure form. Alternatively the probiotics may be cultured on solid media and scraped into a liquid carrier. The resulting product may be spray-dried into a powder form and encapsulated or combined with excipients to be delivered in sachets.

Combinations of Clostridia, *Escherichia coli, Bacteroides,* and *Peptostreptococcus* with or without Lactobacilli, Bifidobacteria and Eubacteria may be used in varying disorders.

Example No 1—43 Year Old Female

Patient with long standing constipation not responsive to high-dose fibre usage together with prokinetics and standard anti-constipation treatments, was treated with increasing doses of orally administered bacterial mix (mixture composition included *Clostridium innocuum, bifermentans, butyricum,* together with *Bacteroides fragilis, thetaiotaomicron* and *uniformis.* Three strains of *Escherichia coli* were also included, as was *Lactobacillus*). This was ingested twice daily in the first two weeks and then daily thereafter. The patient was not given any pre-treatment purgative nor any antibiotics. However, she did take Ranitidine (an acid suppressant) three hours prior to ingestion of the bacterial mix. Two weeks after commencing the treatment the patients constipation—which would prevent her from defecating for up to four days—reversed to increased frequency with reduction of bloating. Initially, gas production increased and there was burbulance and gurgling in the abdomen but after four weeks of treatment the patient was defecating on a daily basis with no sensation of incomplete emptying and an almost total absence of bloating. Following the treatment she remained virtually normal, defecating on a daily basis with 3 month follow up.

Example No 2—4½ Year Old Male

Patient with 3 year history of diagnosis of autism associated with Irritable Bowel Syndrome characterised by constipation alternating with diarrhoea and flatulence, with foul motions, was treated with oral administration of bacterial mix consisting of *Clostridium bifermentans, Clostridium innocuum,* and *Clostridium butyricum* in combination with three strains of *Escherichia coli,* three strains of *bacteroides* and *Peptostreptococcus productus.* These were ingested following acid suppression with Ranitidine and were at first taken 3 times daily, reducing to twice daily and then once daily maintenance for eight weeks. The patient's autistic symptoms were reversed quite dramatically with word power increasing from 20 to 200 words (counted by teacher at special 'autistic' school), he began to sleep through the night, and his IBS-type symptoms reverted to near-normality with less constipation, less diarrhoea and less foul flatulence. He developed eye contact, was able to speak sentences up to six words constructed to commands and he began to look, to the untrained eye, as a relatively normal child by about week 10.

Example 3 Male Child, 5½ Years Old

Male child, 5½ years of age with autism symptoms dating back to age of around 15 months but diagnosed significantly later. The patient presented initially with gastrointestinal symptoms in association with classical autism—for treatment of the bowel symptoms. Although stool test did not indicate any specific pathogen the bowel symptoms resembled those of a chronic infection or adult Irritable Bowel Syndrome (IBS), ie intermittent diarrhoea, constipation, cramping, colicky pain, inability to sleep at night, occasional explosive diarrhoea and incontinence. The patient was treated with orthostatic lavage using sodium pico-sulfate followed by water to produce voluminous diarrhoea and to flush out the enteric contents. He was then given 125 mg Vancomycin three times daily orally followed by oral re-colonisation with bacteria at a concentration of $10^9$ through to $10^{10}$, suspended in yoghurt—of strains which included *bacteroides, Escherichia coli,* and non pathogenic Clostridia—including *Clostridium innocuum, bifermentans* and *ramosum.* The response was quite noticeable, in the reversal of the abnormal stool function towards normality. The patient was also able to sleep through the night without any explosive diarrhoea and produced formed stools within five days of commencing the bacterial therapy. While the bacteriotherapy was continued the bowel symptoms were well controlled. Within 3-4 weeks of missing out the treatment for a week or two some of the symptoms would begin to recur. This suggested that the abnormal bacterial flora was suppressed rather than being cured with this treatment in this patient. The unexpected finding however, was a noticeable and marked reversal of symptoms of autism. Whereas previously repetitive movements were present with lack of eye contact, eye contact returned fairly rapidly together with cessation of repetitive movement and progressive increase of word power from around 20 words to around 600 words by the sixth month of treatment. The therapy continues now for more than 12 months with sustained reversal of autism and IBS symptoms.

Example 4 Male Child, 7 Years Old

A seven year old male patient was referred for treatment initially of bowel problems. He had developed autism between age 1 and 2 years characterised by lack of eye contact, repetitive movements, poorly developed cognitive abilities, vocabulary of fewer than 20 words The marked bowel symptoms were characterised by either constipation or large voluminous motions, sometimes diarrhoea and explosive stools. Stool examination was negative.

The patient was given a pre-treatment of Vancomycin 125 mg twice daily and at one week he was given an orthostatic lavage consisting of picosulfate preparation which flushed out his bowel. He was then given twice daily oral bacteriotherapy consisting of cultures containing living probiotics. These included several *bacteroides* species, *Escherichia coli* and non-pathogenic Clostridia such as *Clostridium butyricum*, *Clostridium bifermentans* and *Clostridium innocuum*. Within two weeks the bowel symptoms reversed to normal defecation with soft, formed stool—once or twice per day. Constipation disappeared, eye contact returned over the next six weeks and vocabulary and word use quite dramatically improved, to everyone's surprise. When followed for eight months over 600 words could be counted in the vocabulary with sentences of up to eight words being constructed where previously this was not possible. Some abstract thinking was noted by teachers at the special autism school. Parents in particular noted reduced aggression, greater co-operation, and general increasing ability to develop a more normal relationship with the child. Repetitive action also disappeared.

Example 5 Male Child, 6 Years Old

A male patient aged 6 was referred to the clinic for treatment of chronic diarrhoea and at times incontinence. The child had been autistic since the age of one year and three months. The diagnosis however was delayed. He had slow cognitive development and very limited vocabulary. There was virtually absent eye contact and at times violent and explosive behaviour. The greatest problem with management was that of control of defecation as the child developed a fascination with the stools which would then be spread over furniture and walls. This brought severe pressure upon the family with respect to difficulty with management. Stool test was collected and again was negative for any pathogen. The patient was given Vancomycin 250 mg twice daily for 10 days after which a polyethylene glycol orthostatic lavage achieved a large volume flush of the bowel. He was then given twice daily oral bacteriotherapy in a neutral yogurt as a carrier. Within one week the bowel function returned to virtual normality. However, the behavioural changes were just as rapid in reversing again characterised by fairly rapid reduction in aggressiveness and uncontrollable behaviour, sleeping through the night, increased eye contact, and progressively increased word power. The behaviour of spreading stools also disappeared, more as a behavioural change than learnt phenomenon. The patient was continued on medications for over a year and progressively improved in all parameters—at times fluctuating in severity.

The invention claimed is:

1. A pharmaceutical composition in a capsule or microcapsule adapted for enteric delivery comprising a plurality of viable non-pathogenic *Clostridium* spores and a plurality of viable non-pathogenic microorganisms from one or more genera selected from the group consisting of *Coprococcus, Dorea, Eubacterium, Gemmiger*, and *Ruminococcus*, wherein said pharmaceutical composition comprises no viable organisms from at least one genus selected from the group consisting of *Lactobacillus* and *Bifidobacterium*.

2. The pharmaceutical composition of claim 1, wherein said pharmaceutical composition comprises no viable organisms from at least one genus selected from the group consisting of *Bacteroides, Fusobacterium, Propionibacterium, Lactobacillus, Escherichia, Desulfomonas, Peptostreptococcus*, and *Bifidobacterium*.

3. The pharmaceutical composition of claim 1, wherein said plurality of viable non-pathogenic microorganisms comprise two or more species selected from the group consisting of *Coprococcus catus, Coprococcus comes, Dorea formicigenerans, Eubacterium eligens, Eubacterium hadrum, Eubacterium hallii, Eubacterium rectale, Gemmiger formicilis*, and *Ruminococcus torques*.

4. The pharmaceutical composition of claim 1, wherein said plurality of viable non-pathogenic microorganisms comprise *Coprococcus*.

5. The pharmaceutical composition of claim 1, wherein said plurality of viable non-pathogenic microorganisms comprise *Dorea*.

6. The pharmaceutical composition of claim 1, wherein said plurality of viable non-pathogenic microorganisms comprise *Eubacterium*.

7. The pharmaceutical composition of claim 1, wherein said plurality of viable non-pathogenic microorganisms comprise *Gemmiger*.

8. The pharmaceutical composition of claim 1, wherein said plurality of viable non-pathogenic microorganisms comprise *Ruminococcus*.

9. The pharmaceutical composition of claim 1, wherein said pharmaceutical composition is formulated as an enteric coated capsule or an enteric coated microcapsule.

10. The pharmaceutical composition of claim 1, wherein said pharmaceutical composition is frozen.

11. The pharmaceutical composition of claim 1, wherein said pharmaceutical composition comprises about $10^9$ to about $10^{11}$ spores or microorganisms.

12. The pharmaceutical composition of claim 1, wherein said pharmaceutical composition comprises about $10^9$ to about $10^{11}$ spores.

13. The pharmaceutical composition of claim 1, wherein said pharmaceutical composition comprises about $10^7$ to about $10^9$ spores or microorganisms.

14. The pharmaceutical composition of claim 1, wherein said pharmaceutical composition comprises about $10^7$ to about $10^9$ spores.

15. The pharmaceutical composition of claim 1, wherein said pharmaceutical composition is lyophilized, pulverized, powdered, or any combination thereof.

16. The pharmaceutical composition of claim 1, wherein said pharmaceutical composition is lyophilized.

17. The pharmaceutical composition of claim 1, wherein said pharmaceutical composition comprises no viable *Lactobacillus*.

18. The pharmaceutical composition of claim 17, wherein said pharmaceutical composition comprises no viable *Bifidobacterium*.

19. The pharmaceutical composition of claim 1, wherein said pharmaceutical composition comprises no viable *Bacteroides*.

20. The pharmaceutical composition of claim 1, wherein said pharmaceutical composition consists essentially of spores.

21. The pharmaceutical composition of claim 1, wherein said *Clostridium* spores are selected from the group consisting of *Clostridium absonum, Clostridium argentinense, Clostridium baratii, Clostridium bifermentans, Clostridium botulinum, Clostridium butyricum, Clostridium cadaveris, Clostridium camis, Clostridium celaturn, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium ramosum, Clostridium sardiniense, Clostridium sartagoforme, Clostridium scindens, Clostridium septicum, Clostridium sordeffii, Clostridium sphenoides, Clostridium spiroforme, Clostridium sporogenes, Clostridium subterminale, Clostridium symbiosum, Clostridium tertium, Clostridium tetani, Clostridium welchii*, and *Clostridium villosum*.

22. The pharmaceutical composition of claim 1, wherein said plurality of viable non-pathogenic microorganisms comprise *Coprococcus, Dorea, Eubacterium, Gemmiger*, and *Ruminococcus*.

23. A pharmaceutical composition in a capsule or microcapsule adapted for enteric delivery comprising a plurality of viable non-pathogenic *Clostridium* spores and a plurality of viable non-pathogenic microorganisms from one or more genera selected from the group consisting of *Gemmiger* and *Ruminococcus*, wherein said pharmaceutical composition does not comprise viable organisms from at least one genus selected from the group consisting of *Lactobacillus* and *Bifidobacterium*.

24. The pharmaceutical composition of claim 23, wherein said plurality of viable non-pathogenic microorganisms comprise both *Gemmiger* and *Ruminococcus*.

25. The pharmaceutical composition of claim 23, wherein said plurality of viable non-pathogenic microorganisms comprise *Gemmiger formicilis* and *Ruminococcus torques*.

26. The pharmaceutical composition of claim 23, wherein said *Clostridium* spores are selected from the group consisting of *Clostridium absonum, Clostridium argentinense, Clostridium baratii, Clostridium bifermentans, Clostridium botulinum, Clostridium butyricum, Clostridium cadaveris, Clostridium camis, Clostridium celaturn, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium ramosum, Clostridium sardiniense, Clostridium sartagoforme, Clostridium scindens, Clostridium septicum, Clostridium sordeffii, Clostridium sphenoides, Clostridium spiroforme, Clostridium sporogenes, Clostridium subterminale, Clostridium symbiosum, Clostridium tertium, Clostridium tetani, Clostridium welchii*, and *Clostridium villosum*.

27. The pharmaceutical composition of claim 23, wherein said pharmaceutical composition is formulated as an enteric coated capsule or an enteric coated microcapsule.

28. The pharmaceutical composition of claim 23, wherein said pharmaceutical composition is frozen.

29. The pharmaceutical composition of claim 23, wherein said pharmaceutical composition comprises about $10^9$ to about $10^{11}$ spores or microorganisms.

30. The pharmaceutical composition of claim 23, wherein said pharmaceutical composition comprises about $10^9$ to about $10^{11}$ spores.

31. The pharmaceutical composition of claim 23, wherein said pharmaceutical composition comprises about $10^7$ to about $10^9$ spores or microorganisms.

32. The pharmaceutical composition of claim 23, wherein said pharmaceutical composition comprises about $10^7$ to about $10^9$ spores.

33. The pharmaceutical composition of claim 23, wherein said pharmaceutical composition is lyophilized, pulverized, powdered, or any combination thereof.

34. The pharmaceutical composition of claim 23, wherein said pharmaceutical composition does not comprise viable *Lactobacillus*.

35. The pharmaceutical composition of claim 23, wherein said pharmaceutical composition does not comprise viable *Bifidobacterium*.

36. The pharmaceutical composition of claim 23, wherein said pharmaceutical composition does not comprise viable *Bacteroides*.

37. The pharmaceutical composition of claim 23, wherein said pharmaceutical composition consists essentially of spores.

* * * * *